United States Patent
Zhao et al.

(10) Patent No.: US 12,054,653 B2
(45) Date of Patent: Aug. 6, 2024

(54) ADHESIVE MATERIAL WITH TRIGGERABLE ON-DEMAND DETACHMENT

(71) Applicant: Massachusetts Institute of Technology, Cambridge, MA (US)

(72) Inventors: Xuanhe Zhao, Allston, MA (US); Hyunwoo Yuk, Cambridge, MA (US); Xiaoyu Chen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 198 days.

(21) Appl. No.: 17/327,944

(22) Filed: May 24, 2021

(65) Prior Publication Data

US 2021/0380848 A1    Dec. 9, 2021

Related U.S. Application Data

(60) Provisional application No. 63/034,644, filed on Jun. 4, 2020.

(51) Int. Cl.
*C09J 7/32* (2018.01)
*A61L 24/00* (2006.01)
(Continued)

(52) U.S. Cl.
CPC ............. *C09J 7/32* (2018.01); *A61L 24/0031* (2013.01); *C08K 5/0025* (2013.01); *C09J 7/20* (2018.01); *C09J 105/00* (2013.01); *C09J 109/04* (2013.01); *C09J 125/08* (2013.01); *C09J 129/04* (2013.01); *C09J 133/064* (2013.01);
(Continued)

(58) Field of Classification Search
None
See application file for complete search history.

(56) References Cited

U.S. PATENT DOCUMENTS

| | | |
|---|---|---|
| 2004/0170663 A1 | 9/2004 | Wang et al. |
| 2017/0266337 A1 | 9/2017 | Hoogenboom et al. |
| (Continued) | | |

FOREIGN PATENT DOCUMENTS

| | | |
|---|---|---|
| WO | 2018150186 | 8/2018 |
| WO | 2019195324 | 10/2019 |

OTHER PUBLICATIONS

International Search Report and Written Opinion for PCT/US21/33817, dated Oct. 4, 2021.
(Continued)

*Primary Examiner* — Frank D Ducheneaux
(74) *Attorney, Agent, or Firm* — Nieves IP Law Group, LLC; Peter A. Nieves

(57) ABSTRACT

An adhesive material that provides fast and robust adhesion on wet surfaces, where the adhesion formed is detachable on-demand. The adhesive material is formed of one or more hydrophilic polymers or copolymers grafted with one or more amine coupling groups via a plurality of cleavable physical bonds and/or cleavable covalent bonds and one or more cross linkers. Application of the adhesive material on a wet surface causes the adhesive material to absorb liquid to thereby swell the adhesive material to form a layer of hydrogel, resulting in the formation of temporary crosslinks followed by covalent crosslinks with the surface. Introducing a triggering agent cleaves the cleavable physical bonds and/or cleavable covalent bonds to allow for non-traumatic detachment of the adhesive material from the surface.

15 Claims, 16 Drawing Sheets

(51) Int. Cl.

| | |
|---|---|
| *C08K 5/00* | (2006.01) |
| *C09J 7/20* | (2018.01) |
| *C09J 105/00* | (2006.01) |
| *C09J 109/04* | (2006.01) |
| *C09J 125/08* | (2006.01) |
| *C09J 129/04* | (2006.01) |
| *C09J 133/06* | (2006.01) |
| *C09J 133/10* | (2006.01) |
| *C09J 133/26* | (2006.01) |
| *C09J 151/00* | (2006.01) |
| *C09J 175/00* | (2006.01) |
| *C09J 181/08* | (2006.01) |

(52) U.S. Cl.
CPC ......... *C09J 133/066* (2013.01); *C09J 133/10* (2013.01); *C09J 133/26* (2013.01); *C09J 151/003* (2013.01); *C09J 175/00* (2013.01); *C09J 181/08* (2013.01); *C09J 2301/10* (2020.08); *C09J 2301/306* (2020.08); *C09J 2301/502* (2020.08); *C09J 2405/00* (2013.01); *C09J 2429/00* (2013.01); *C09J 2433/00* (2013.01); *C09J 2451/00* (2013.01); *C09J 2475/00* (2013.01)

(56) References Cited

U.S. PATENT DOCUMENTS

2019/0091367 A1   3/2019   Li et al.
2020/0353120 A1   11/2020  Zhao et al.

OTHER PUBLICATIONS

Hu, et al; Cyclodextrin-Based Host-Guest Supramolecular Nanoparticles for Delivery: From Design to Applications; 2014 American Chemical Society; Acc. Chem. Res. 2014 47-2014-2025.

Vakalopoulos, K. A. et al. Mechanical strength and rheological properties of tissue adhesives with regard to colorectal anastomosis: an ex vivo study. Annals of Surgery 261, 323-331 (2015).

Rose, S. et al. Nanoparticle solutions as adhesives for gels and biological tissues. Nature 505, 382-385 (2014).

Lee, B. P., Messersmith, P. B., Israelachvili, J. N. & Waite, J. H. Mussel-inspired adhesives and coatings. Annual Review of Materials Research 41, 99-132 (2011).

Cyanoacrylate adhesives have been found to further suffer from high cytotoxicity and inflexibility after curing (See Annabi, N., Yue, K., Tamayol, A. & Khademhosseini, A. Elastic sealants for surgical applications. European Journal of Pharmaceutics and Biopharmaceutics 95, 27-39 (2015).

Karp, J. M. A Slick and Stretchable Surgical Adhesive. New England Journal of Medicine 377, 2092-2094 (2017).

Li, J. et al. Tough adhesives for diverse wet surfaces. Science 357, 378-381 (2017).

Host: αCD

Guest 1: n-butyl (n-Bu) group

Guest 2: Adamantyl group

Guest 3: Benzyl group

Bond cleavage triggers for Guest 1-3:
• Free guests (e.g., free Amantadine solution)

Guest 4: Trans-Azobenzene group

Bond cleavage triggers for Guest 4:
• Heat
• UV irradiation
• Free guests (e.g., free Amantadine solution)

FIG 2B

Host: βCD

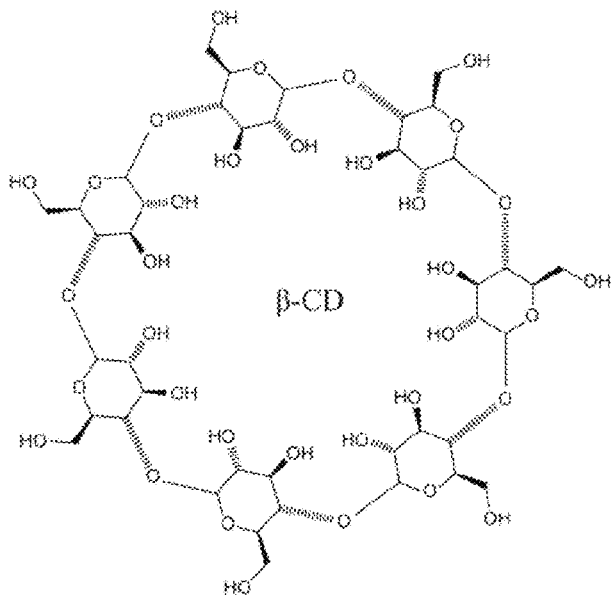

β-CD

Guest 1: n-butyl (n-Bu) group

Guest 2: Adamantyl group

Guest 3: Benzyl group

Guest 4: Cyclohexyl(ester) group

Guest 5: Cyclododecyl(amide) group

Guest 6: 2-Naphthylmethyl group

Guest 7: 1-Pyrenylmethyl group

Bond cleavage triggers for Guest 1-7:
•Free guests (e.g., free Amantadine solution)

Guest 8: Ferrocene group

Bond cleavage triggers for Guest 8:
•Reduction agents (e.g., Dithiothreitol (DTT), tris(2-carboxyethyl)phosphine (TCEP), Glutathione (GSH))
•Free guests (e.g., free Amantadine solution)

Guest 9: Trans-Azobenzene group

Bond cleavage triggers for Guest 9:
•Heat
•UV irradiation
•Free guests (e.g., free Amantadine solution)

Host: γCD

Guest 1: Benzyl group

Guest 2: Cyclododecyl(amide) group

Guest 3: 2-Naphthylmethyl group

Guest 4: 1-Pyrenylmethyl group

Guest 5: 9-Phenanthrylmethyl group

Bond cleavage triggers for Guest 1-5:
•Free guests (e.g., free Amantadine solution)

ADHESIVE MATERIAL WITH TRIGGERABLE ON-DEMAND DETACHMENT

CROSS-REFERENCE TO RELATED APPLICATIONS

This application claims the benefit of U.S. Provisional Patent Application Ser. No. 63/034,644, filed Jun. 4, 2020, entitled "Body Fluid Resistant Tissue Adhesives," which is incorporated by reference herein in its entirety.

GOVERNMENT SUPPORT STATEMENT

This invention was made with Government support under Grant No. EFMA-1935291 awarded by the National Science Foundation. The Government has certain rights in the invention.

FIELD OF THE INVENTION

The present invention generally relates to adhesive materials and methods for adhering surfaces, and more particularly to a dry bioadhesive material and methods for adhering wet tissue surfaces, wherein the adhesion formed between the adhesive material and the surfaces is detachable on-demand.

BACKGROUND OF THE INVENTION

Each year, millions of major surgeries are performed worldwide. Whereas sutures and staples are most commonly used in these surgeries to close wounds, achieve hemostasis, and attach implantable devices on tissue, bioadhesives (e.g., tissue adhesives, hemostatic agents, and tissue sealants) have been considered as an alternative because of their potential advantages such as ease of use, air- or water-tight sealing, and potential to reduce tissue damage. However, existing bioadhesives display several limitations.

It is generally understood that two dry surfaces can instantly adhere upon contact with each other by intermolecular forces such as hydrogen bonds, electrostatic and van der Waals interactions. However, it is extremely challenging to form such instant adhesion between wet surfaces, such as biological tissues, because water separates molecules from the two surfaces to form instant interactions that impede adhesion between the surfaces.

Further, existing tissue adhesives, mostly in the form of liquids or wet hydrogels, face many limitations including weak bonding, low biocompatibility, and poor mechanical match with tissues. In particular, as depicted in FIGS. 1A-1B, such existing tissue adhesives rely on diffusion of their molecules (e.g., mono/macromers or polymers) into the polymer networks of the tissues for bonding, which can take significant time and provides weak adhesion, and wherein the presence of interfacial liquid between the adhesive and the tissues further interferes with the adhesion process.

For example, commercially available adhesives (e.g., fibrin glues, albumin-based adhesives, polyethylene glycol-based adhesives), nanoparticle solutions, and mussel-inspired adhesives exhibit slow adhesion formation (longer than 1 min) and weak adhesion on wet surfaces (interfacial toughness less than 20 J m$^{-2}$)(See Vakalopoulos, K. A. et al. Mechanical strength and rheological properties of tissue adhesives with regard to colorectal anastomosis: an ex vivo study. *Annals of Surgery* 261, 323-331 (2015); Rose, S. et al. Nanoparticle solutions as adhesives for gels and biological tissues. *Nature* 505, 382-385 (2014); Lee, B. P., Messersmith, P. B., Israelachvili, J. N. & Waite, J. H. Mussel-inspired adhesives and coatings. *Annual Review of Materials Research* 41, 99-132 (2011)). Cyanoacrylate adhesives have been found to further suffer from high cytotoxicity and inflexibility after curing (See Annabi, N., Yue, K., Tamayol, A. & Khademhosseini, A. Elastic sealants for surgical applications. *European Journal of Pharmaceutics and Biopharmaceutics* 95, 27-39 (2015); Karp, J. M. A Slick and Stretchable Surgical Adhesive. *New England Journal of Medicine* 377, 2092-2094 (2017)). Adhesion of bulk hydrogels on tissues having interfacial toughness on the order of 100 to 1,000 J m$^{-2}$ has been reported, but such hydrogels require prolonged pressure application of at least 10 min up to 30 min to form the adhesion (See Li, J. et al. Tough adhesives for diverse wet surfaces. *Science* 357, 378-381 (2017)).

Further, during medical procedures, it might be critical to reposition a misplaced adhesive or to retrieve an implanted device held in place with an adhesive. However, few reversible adhesives have been developed, which all possess serious drawbacks. Most of the adhesives commonly rely on harsh non-biocompatible triggering conditions such as concentrated metallic ions, heat, or ultraviolet (UV) irradiation for their detachment, which is unfavorable for the adhesives, the tissue(s) on which they are attached, and adjacent native tissues.

In view of the great potential for tissue adhesives, particularly in medical applications, improvements are greatly needed.

SUMMARY OF THE INVENTION

According to one aspect, the present invention provides an adhesive material for adhering one or more wet surfaces and for triggerable detachment from the one or more surfaces comprising: (i) one or more hydrophilic polymers or copolymers, grafted with (ii) one or more amine coupling groups via (iii) a plurality of cleavable physical bonds and/or cleavable covalent bonds, and (iv) one or more cross linkers, wherein the adhesive material is in the form of a film or tape having a top surface and a bottom surface, and wherein the adhesive material has a liquid content such that placement of one or more of the top and/or bottom surfaces of the adhesive material in contact with the one or more wet surfaces causes the adhesive material to absorb liquid from the one or more wet surfaces, swell to form temporary crosslinking between the dry adhesive material and the wet surface, and form covalent bonds between the one or more amine coupling groups and the one or more wet surfaces.

Embodiments according to this aspect can include one or more of the following features. The (i) one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, pectin, and combinations thereof. The (ii) one or more amine coupling groups are selected from N-hydroxysuccinimide ester, N-hydroxysulfosuccinimide ester, aldehyde, imidoester, epoxide, isocyanate, catechol, and combinations thereof. The (iii) cleavable physical bonds are selected from hydrogen bonds, electrostatic bonds, and host-guest bonds, and the cleavable covalent bonds are selected from boron-oxygen bonds, phenylboronate ester, disulfide bonds, hydrazone bonds, imine bonds, Diels-Alder bonds, carbon-carbon/carbon-sulfur bonds, and oxime bonds. The host-guest bonds are selected from αCyclodextrin (CD) as a host and n-butyl (n-Bu), Adamantyl, Benzyl, and Trans-Azobenzene groups as a guest; βCD as a host and Adamantyl, t-butyl, Cyclohexyl(ester), Cyclododecyl(amide), Benzyl, 2-Naphthylmethyl, 1-Pyrenylmethyl, Ferrocene, Trans-Azobenzene groups as a guest; and γCD as a host and Cyclododecyl, Benzyl, 2-Naphthylmethyl, 9-Phenanthrylmethyl, and 1-Pyrenylmethyl groups as a guest. The (iv) one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The adhesive material comprises interpenetrating networks of (i) polyvinyl alcohol (PVA) and poly(acrylic acid) (PAA) grafted with (ii) N-hydroxysuccinimide (NHS) ester via (iii) cleavable disulfide bonds in the dry state. Negatively charged carboxylic acid groups in the poly (acrylic acid) grafted with N-hydroxysuccinimide ester facilitate absorption of liquid and swelling of the dry adhesive material and further form intermolecular bonds with the one or more wet tissue surfaces within less than 60 seconds after contact between the dry adhesive material and the one or more wet surfaces. The N-hydroxysuccinimide ester grafted in the poly(acrylic acid) forms cleavable covalent bonds with primary amine groups present on the one or more wet surfaces. After the covalent crosslinking is formed between the one or more amine coupling groups and the one or more wet surfaces, the swollen adhesive material transforms into a layer of a hydrogel. The hydrogel has a fracture toughness of at least about 1,000 J m$^{-2}$. The adhesive material is in the form of a flat sheet, a perforated sheet, a double sided tape or film, or a perforated double sided tape or film. The adhesive material comprises a top surface and a bottom surface, and wherein adhesive material further comprises one or more backing material layers disposed on at least one of the top surface and bottom surface. The adhesive material further comprises one or more engineering solids, and/or devices adhered to one or more surfaces of the adhesive material. The adhesive material is biodegradable.

According to another aspect, the present invention provides a method of adhering wet tissues using an adhesive material and on-demand removal of the adhesive material comprising: providing the adhesive material comprising (i) one or more hydrophilic polymers or copolymers, grafted with (ii) one or more amine coupling groups via (iii) a plurality of cleavable physical bonds and/or cleavable covalent bonds, and (iv) one or more cross linkers; placing the adhesive material in contact with one more wet surfaces of the wet tissue; allowing the adhesive material to absorb liquid from the one or more wet surfaces to thereby swell the adhesive material to form a layer of hydrogel; allowing temporary crosslinking to form between the adhesive material and the surface; optionally allowing covalent bonds to form between the one or more amine coupling groups and the one or more wet surfaces; under physiological conditions, introducing a triggering agent to cleave the cleavable physical bonds and/or cleavable covalent bonds; and detaching the adhesive material from the one or more surfaces.

Embodiments according to this aspect can include one or more of the following features. The (i) one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, pectin, and combinations thereof. The (ii) one or more amine coupling groups are selected from N-hydroxysuccinimide ester, N-hydroxysulfosuccinimide ester, aldehyde, imidoester, epoxide, isocyanate, catechol, and combinations thereof. The (iii) cleavable physical bonds are selected from hydrogen bonds, electrostatic bonds, and host-guest bonds, and the cleavable covalent bonds are selected from boron-oxygen bonds, phenylboronate ester, disulfide bonds, hydrazone bonds, imine bonds, Diels-Alder bonds, carbon-carbon/carbon-sulfur bonds, and oxime bonds. The host-guest bonds are selected from αCyclodextrin(CD) as a host and n-butyl (n-Bu), Adamantyl, Benzyl, and Trans-Azobenzene groups as a guest; βCD as a host and Adamantyl, t-butyl, Cyclohexyl(ester), Cyclododecyl(amide), Benzyl, 2-Naphthylmethyl, 1-Pyrenylmethyl, Ferrocene, Trans-Azobenzene groups as a guest; and γCD as a host and Cyclododecyl, Benzyl, 2-Naphthylmethyl, 9-Phenanthrylmethyl, and 1-Pyrenylmethyl groups as a guest. The (iv) one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof. The adhesive material comprises interpenetrating networks of (i) polyvinyl alcohol (PVA) and poly(acrylic acid) (PAA) grafted with (ii) N-hydroxysuccinimide (NHS) ester via (iii) cleavable disulfide bonds in the dry state. The PVA and PAA networks absorb the liquid to dry the one or more wet surfaces under a pressure no greater than about 1 kPa applied for no greater than 5 seconds, wherein the PAA network provides carboxylic acid groups that form instant physical crosslinks via hydrogen bonds with the one or more surfaces, and optionally wherein cleavable NHS ester groups grafted to the PAA network forms stable covalent crosslinks with primary amine groups on the one or more surfaces. A pH-dependent de-crosslinking triggering agent is used to cleave the physical bonds. The pH-dependent de-crosslinking triggering agent is sodium bicarbonate. A biocompatible reducing agent is used to cleave the covalent bonds. The biocompatible reducing agent is glutathione. The triggering agent comprises a solution containing a combination of sodium bicarbonate and glutathione.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIGS. 2A-C illustrate examples of cleavable host-guest physical bonds according to embodiments of the present invention, with FIG. 2A illustrating guests for αCD host and corresponding bond cleavage triggers, FIG. 2B illustrating guests for βCD host and corresponding bond cleavage triggers, and FIG. 2C illustrating guests for γCD host and corresponding bond cleavage triggers.

DETAILED DESCRIPTION

Figure 1:
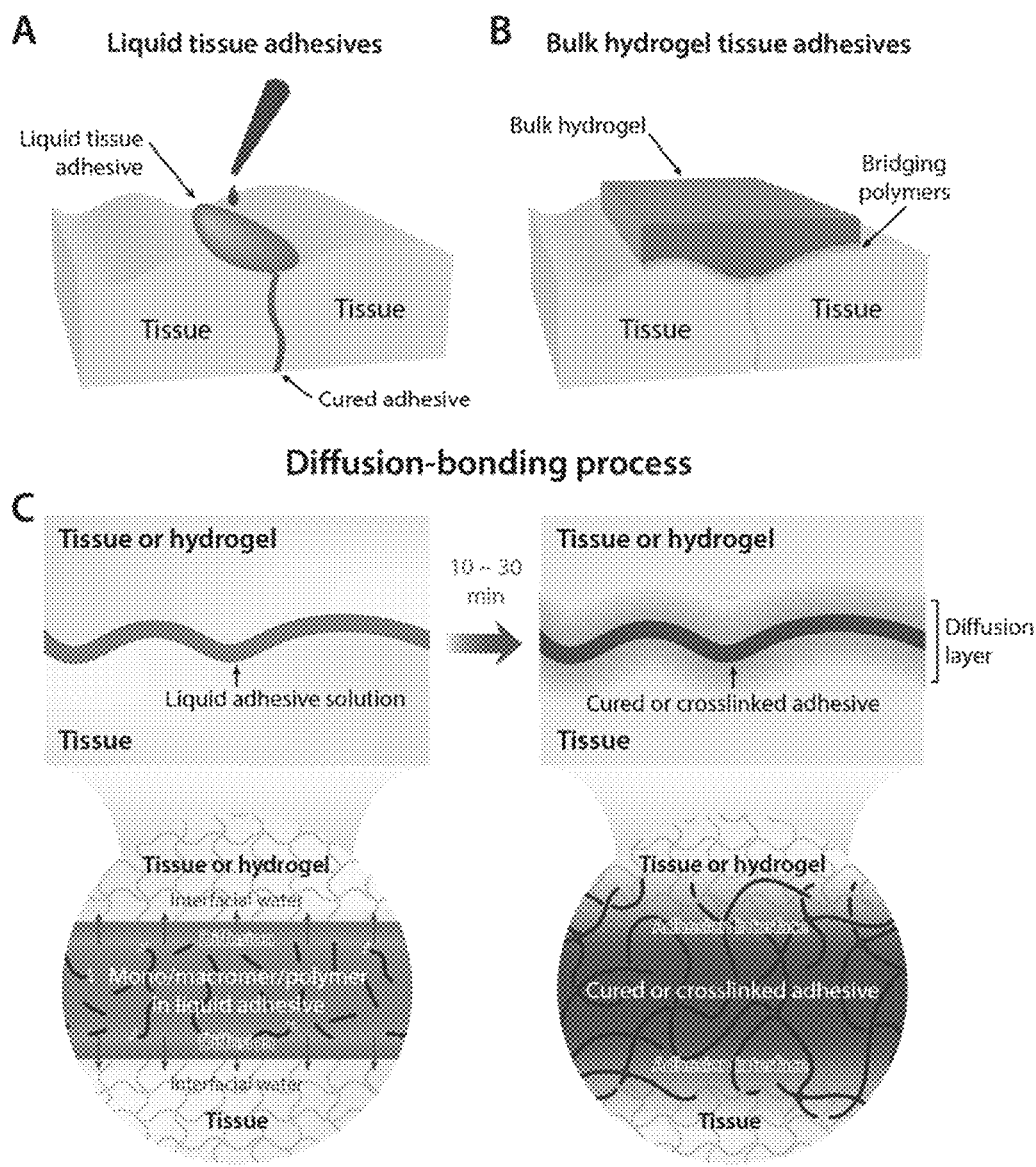
FIGS. 1A-C schematically illustrate tissue adhesives according to the prior art, with FIG. 1A depicting an existing tissue adhesive in the form of liquid, FIG. 1B depicting an existing tissue adhesives in the form of a wet hydrogel, and FIG. 1C depicting a schematic for the mechanism of existing tissue adhesives which relies on diffusion of monomers or polymers into the polymer network of tissues for bonding.
Figure 2A:
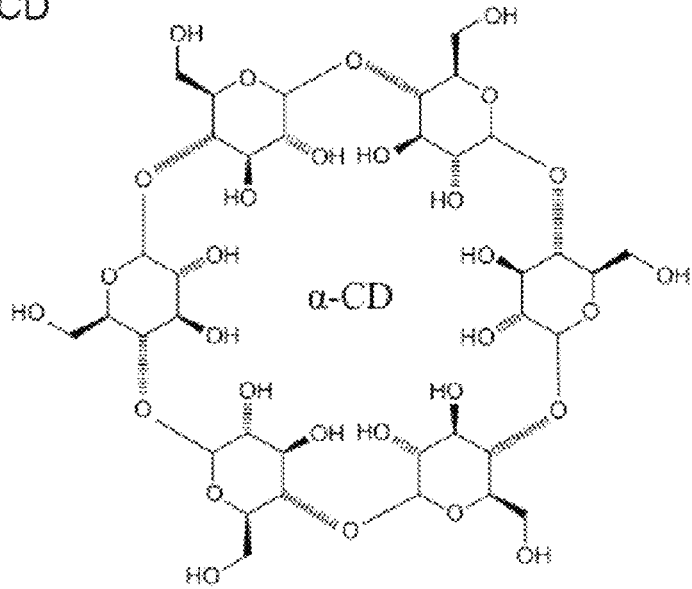
Figure 2A:
Figure 2A:
Figure 2A:
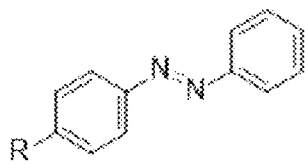
Figure 2C:
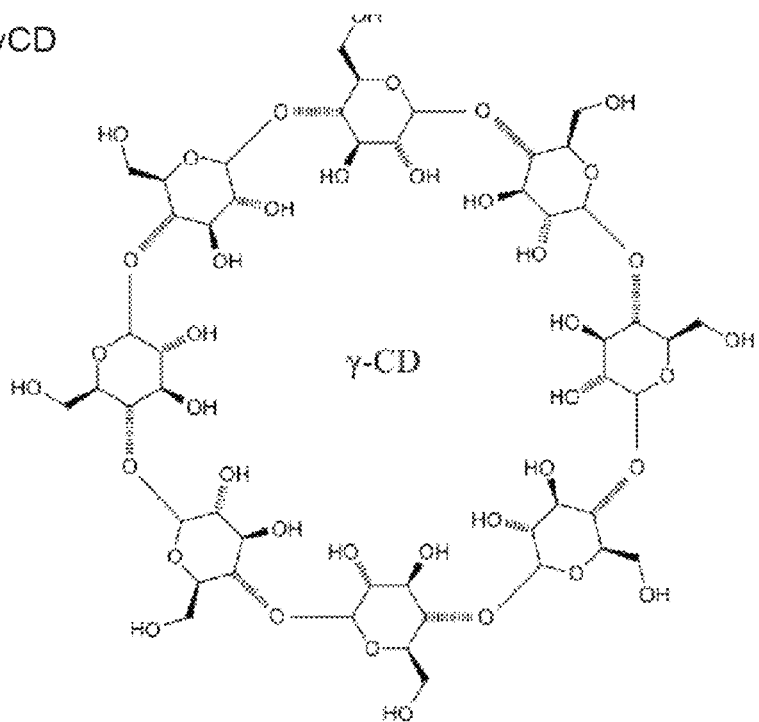
Figure 2C:
Figure 2C:
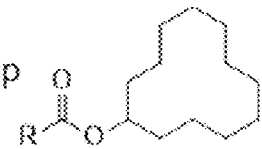
Figure 2C:
Figure 2C:
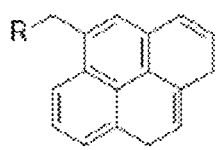
Figure 2C:
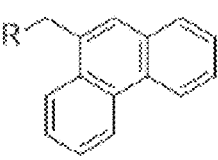
Figure 3:
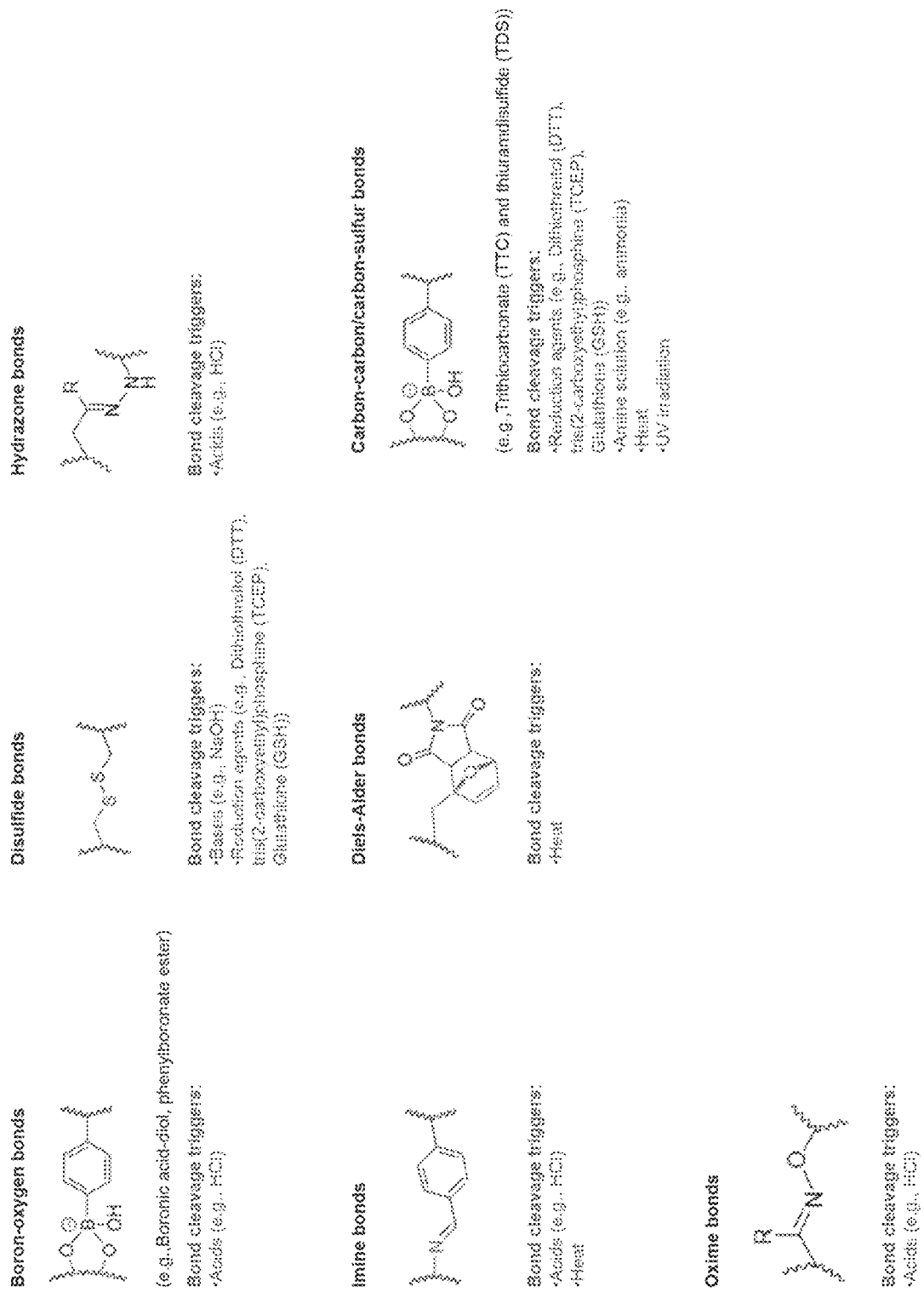
FIG. 3 illustrates examples of cleavable covalent bonds and corresponding bond cleavage triggers according to embodiments of the present invention.

The following definitions are useful for interpreting terms applied to features of the embodiments disclosed herein, and are meant only to define elements within the disclosure.

As used herein, the term "dry" when describing the adhesive material of the present invention refers to a material that is below the equilibrium moisture content of the material in use. As such, when a dry adhesive material of the present invention is placed in contact with a wet tissue or other wet or wetted (e.g., wetted by saline) surface to which it will adhere, the material will absorb fluid (e.g., water, saline, moisture, and physiological body fluids such as blood plasma, interstitial fluid, lymphatic fluid, cerebrospinal fluid, and gastrointestinal fluid) from the wet or wetted surface. Generally, a dry adhesive material will have less than about 50% by weight of liquid components based on total weight of the dry adhesive material.

As used herein, the term "absorb" when describing the mechanism by which the dry adhesive material absorbs water, saline, moisture, and physiological body fluids such as blood plasma, interstitial fluid, lymphatic fluid, cerebrospinal fluid, and gastrointestinal fluid from a wet surface in which it is placed in contact with, refers to atoms or molecules from the liquid of the wet surface crossing the surface of and entering the dry adhesive material.

As used herein, the term "tape" or "film" when describing the adhesive material of the present invention refers to a structure that has a relatively large area as compared to thickness. Such a structure provides flexibility.

As used herein, the term "double sided" when describing the adhesive material of the present invention refers to the adhesive tape or film that provides adhesive properties on both top and bottom sides of the adhesive. It is noted that while the adhesive material may be referred to as double sided, the adhesive properties of a single side or of both sides of the adhesive material may be utilized in a given application. For example, during use, it may be desirable to utilize the adhesive properties of only one side of the adhesive material, while the adhesive properties of a second side may not be utilized (e.g., by maintaining a material layer or backing material disposed upon the second side surface during use so as to block the adhesive properties on that second side). In such an example, the material layer or backing material may initially be disposed upon both the first and second sides, with the material layer or backing material being removed from only the first side prior to application to enable use of the adhesive properties of the first side only.

As used herein, the term "wet tissue" refers to the biological tissue that contains or is covered (partially or fully covered) with fluid including water, saline, moisture, and physiological body fluids such as blood plasma, interstitial fluid, lymphatic fluid, cerebrospinal fluid, and gastrointestinal fluid.

As used herein, the term "instant" when used to describe the instant temporary crosslinks between the adhesive material and one or more wet surfaces refers to a time elapse from the instant that the adhesive material makes contact with the one or more wet surfaces of greater than zero seconds and up to or within about one minute, more preferably less than or equal to about 50 seconds, more preferably less than or equal to about 40 seconds, more preferably less than or equal to about 30 seconds, more preferably less than or equal to about 20 seconds, more preferably less than or equal to about 15 seconds, more preferably less than or equal to about 10 seconds, more preferably less than or equal to about 9 seconds, more preferably less than or equal to about 8 seconds, more preferably less than or equal to about 7 seconds, more preferably less than or equal to about 6 seconds, and more preferably less than or equal to about 5 seconds.

As used herein, the term "temporary" when used to describe the instant temporary crosslinks between the adhesive material and one or more wet surfaces refers to a time range extending between time at which the instant temporary crosslinks form and the sufficiently long time such as over 24 hours after which the instant temporary crosslinks form.

As used herein, "fast" or "quick" when used to describe the fast covalent cross linking between the adhesive material and one or more wet surfaces refers to a time elapse from the instant that the adhesive material makes contact with the one or more wet surfaces of greater than zero seconds and up to and including 5 minutes, more preferably less than or equal to about 4.5 minutes, more preferably less than or equal to about 4 minutes, more preferably less than or equal to about 3.5 minutes, more preferably less than or equal to about 3 minutes, more preferably less than or equal to about 2.5 minutes, more preferably less than or equal to about 2 minutes, more preferably less than or equal to about 1.5 minutes, and more preferably less than or equal to about 1 minute.

As used herein, "swelling" when used to describe the dry adhesive material absorption and swelling upon contact with one or more wet surfaces generally refers to an increase in size by the dry adhesive material. The dry adhesive material is generally in the form of a tape or film, which becomes thicker upon uptake of liquid.

As used herein, "biodegradable" when used to describe the adhesive material refers the decomposition and/or subsequent removal of the implanted material in part or whole within the living animals by the endogenous enzymes and/or water inside the animals.

As used herein, "engineering solids" refers to solid materials that are not biological tissues including synthetic materials such as plastics, metals, glass, ceramics, and elastomers as well as biomaterials processed from natural sources.

As used herein, "on-demand" when used to refer to on-demand removal of the adhesive material from the one or more surfaces to which the adhesive material is attached, refers to removal at any time desired after application of the adhesive material to the target surface, and is accomplished by application of or introduction of a triggering mechanism to the adhesive material, the surface, and/or between the surface and the adhesive material. The triggering mechanism acts to cleave the crosslinks between the adhesive material and the one or more surfaces. In particular, upon application of or introduction of the triggering mechanism, the adhesive material can be removed from the surface with little to no trauma to the surface within about 20 minutes, more preferably within about 10 minutes, more preferably within about 5 minutes by simply grasping the adhesive material (e.g., with tweezers or the like) and pulling the adhesive material from the surface.

Figure 4A:
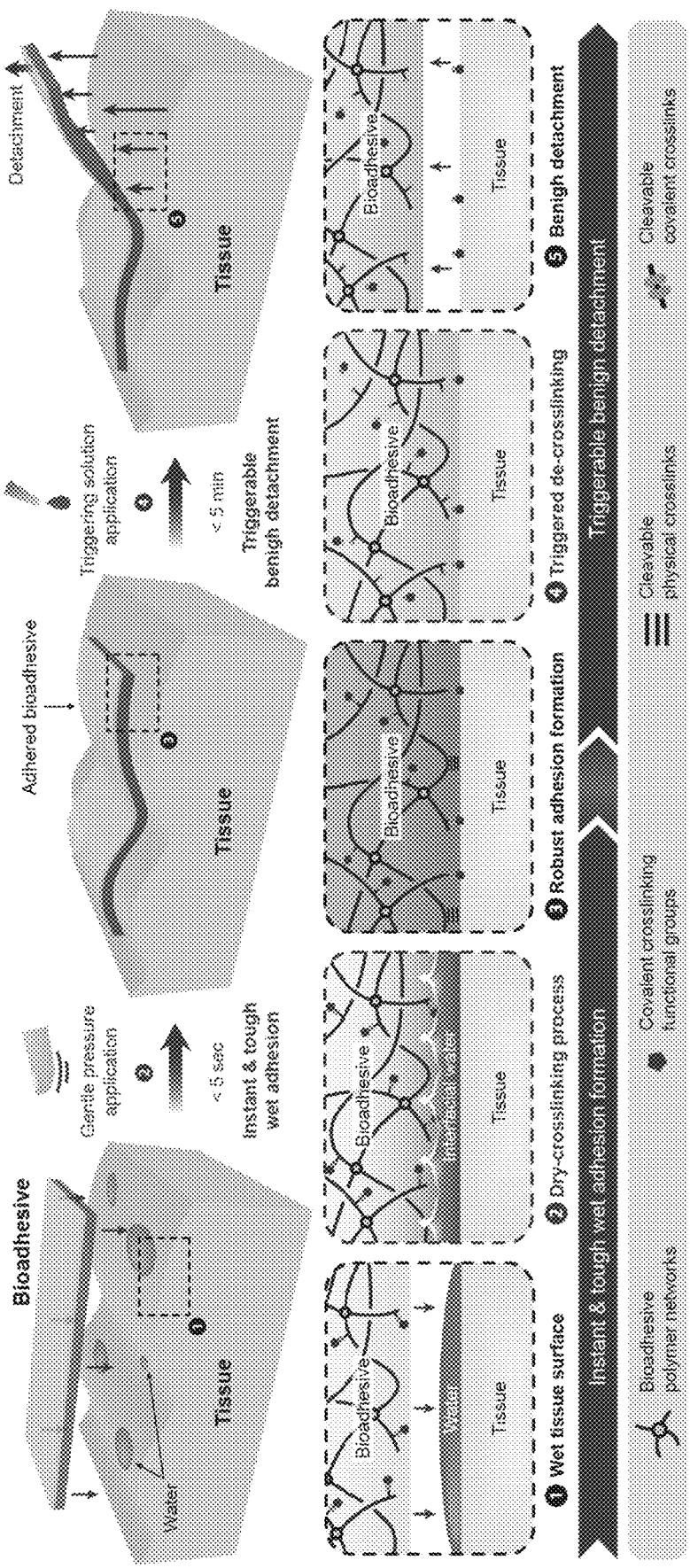
FIGS. 4A-C schematically illustrate the design and mechanisms of instant, tough, and triggerably detachable bioadhesives according to embodiments of the present invention, with FIG. 4A schematically illustrating a design of the bioadhesive and dry-crosslinking and triggerable detachment mechanisms, FIG. 4B schematically illustrating a de-crosslinking process of cleavable physical crosslinks by sodium bicarbonate, and FIG. 4C schematically illustrating a de-crosslinking process of cleavable covalent crosslinks by glutathione.
Figure 4B:
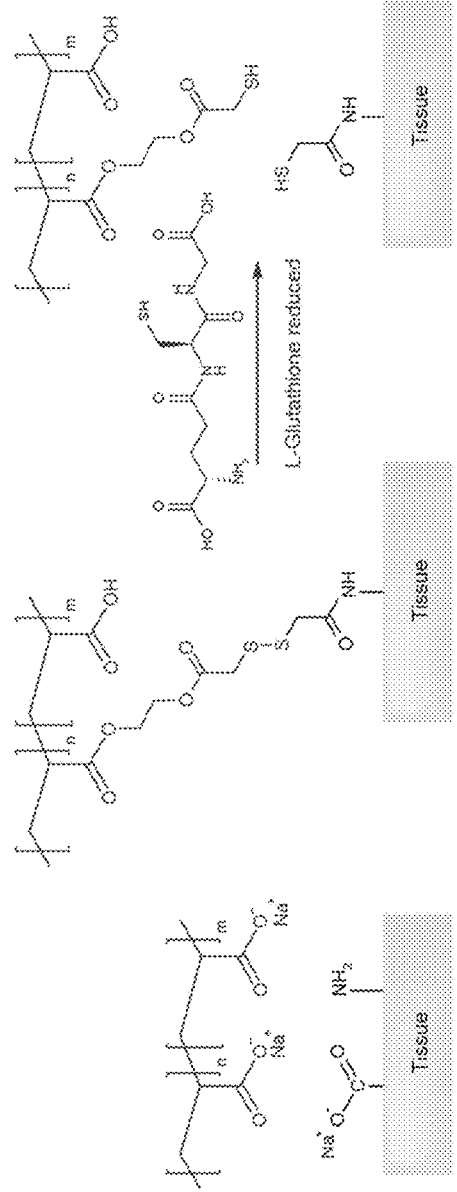

The present invention generally provides an adhesive material that is capable of adhering to wet surfaces and adhering wet surfaces together, particularly wet tissue surfaces. The adhesive material is a dry adhesive material fabricated so as to provide a dry-crosslinking mechanism for instant strong adhesion of wet surfaces. In particular, the dry adhesive material is fabricated such that, when placed into contact with one or more wet surface, it absorbs liquid from the one or more wet surfaces, which swells the adhesive material. This absorption of interfacial liquid allows instant crosslinking by intermolecular interactions between the adhesive material and the one or more wet surfaces, followed by quick covalent crosslinking between the adhesive material and the one or more wet surfaces (see FIGS. 4A-B). As shown in FIGS. 4A-B, the cleavable physical and covalent crosslinks are disposed between the hydrophilic polymers/copolymers and the chemical groups that form crosslinks with the one or more wet surfaces. In addition to forming instant strong adhesion on various wet dynamic tissues, the present adhesive material is detachable from the adhered surface(s) on-demand through the use of a triggering material. In particular, the adhesive material is detachable from the adhered surface(s) at any time desired via a triggering mechanism, particularly a biocompatible trigger. For example, by contacting the adhesive material with the triggering mechanism, the triggering mechanism acts to cleave the cleavable physical and covalent crosslinks (e.g., as shown in FIGS. 4A-B), thereby allowing for detachment of the adhesive material from the surface(s).

The present invention adhesive material thereby overcomes the above-mentioned limitations of the existing adhesive materials (as further depicted in FIGS. 1A-C). Rather than diffusing molecules towards tissues as required by the existing adhesive materials, the present dry adhesive material achieves instant strong adhesion to wet surfaces by synergistically combining drying of interfacial liquid by swelling of the dry adhesive material, instant temporary crosslinking, and fast covalent crosslinking between the adhesive material and the one or more wet surfaces. The present invention adhesive material further provides for on-demand detachment from surfaces to which it is adhered through the use of an adhesion structure and triggering mechanism which reduces tissue trauma and also eliminates the need for harsh non-biocompatible triggering conditions for removal (e.g., concentrated metallic ions, heat, and ultraviolet (UV) irradiation).

As described further below, ex vivo and in vitro models demonstrated that the present adhesive material is capable of achieving strong adhesion between diverse wet dynamic tissues (e.g., skin, tendon, stomach, muscle, heart, and liver) and engineering solids within seconds (e.g, within 5 seconds) with high interfacial toughness (e.g., over 400 J m$^{-2}$, over 500 J m$^{-2}$, over 600 J m$^{-2}$, over 700 J m$^{-2}$, over 800 J m$^{-2}$, over 900 J m$^{-2}$, and even over 1000 J m$^{-2}$), while providing low shear modulus (for example, about 20 kPa or less, about 15 kPa or less, and even about 10 kPa, shear and tensile strengths on the order of about 160 kPa, and high stretchability (e.g., on the order of 7 times, 8 times, 9 times, and even 10 times the original unstretched size), which are comparable to properties found in biological tissues, high biocompatibility and controllable biodegradation. As further demonstrated, at any point after adhesion, the adhesive material can be easily removed through the use of a triggering mechanism.

As such, the present dry adhesive material provides not only a new paradigm in wet adhesion that enables new opportunities in applications as diverse as tissue adhesives, bioscaffolds, drug delivery, and wearable and implantable devices, but also further provides for on-demand, non-traumatic removal.

Reference will now be made in detail to embodiments of the present invention, examples of which are illustrated in the accompanying drawings. Wherever possible, the same reference numbers are used in the drawings and the description to refer to the same or like parts.

According to one aspect, the present invention provides an adhesive material comprising a combination of: (i) one or more hydrophilic polymers or copolymers, grafted with (ii) one or more amine coupling groups via (iii) cleavable physical bonds and/or cleavable covalent bonds, and (iv) one or more cross linkers.

The adhesive material is generally in the form of a dry material in that, when it is placed into contact with one or more wet surfaces such as wet tissue, it absorbs liquid from the one or more wet surfaces, removing the interfacial liquid present between the adhesive material and the wet surfaces. This liquid absorption causes the dry material to swell. Absorption of liquid and swelling of the dry adhesive material provides instant temporary crosslinking between the adhesive material and the wet surface, and further allows for fast subsequent covalent coupling or crosslinking between the adhesive material and the one or more wet surfaces as further described herein.

According to embodiments of the present invention, the (i) one or more hydrophilic polymers or copolymers are selected from any conventional hydrophilic polymers that absorb water at a dry state, including, but not limited to polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, pectin, and combinations thereof). Because the present adhesive material can be used in a wide variety of biomedical applications, the polymers and copolymers used in the present invention are preferably biocompatible (although for non-biomedical applications it would not be necessary to utilize only biocompatible polymer materials). According to preferred embodiments, the one or more hydrophilic polymers contain one or more negatively-charged groups such as poly (acrylic acid), casein, albumin, and alginic acid, whose negatively-charged groups endow hygroscopic properties that are desirable for rapid absorption and removal of interfacial liquid on wet surfaces.

According to embodiments of the present invention, the (ii) one or more amine coupling groups are selected from conventional amine coupling groups, including but not limited to, N-hydroxysuccinimide ester, N-hydroxysulfosuccinimide ester, aldehyde, imidoester, epoxide, isocyanate, catechol, and combinations thereof. Because the present adhesive material can be used in a wide variety of biomedical applications, the amine coupling groups used in the present invention are preferably biocompatible (although for non-biomedical applications it would not be necessary to utilize only biocompatible amine coupling groups). Such amine coupling groups are configured such that the one or more hydrophilic polymers can be grafted with the one or more amine-coupling groups via the cleavable bonds, and such that the one or more amine coupling groups subsequently form covalent crosslinks with the wet surface on which the adhesive material is used.

According to embodiments of the present invention, the (iii) cleavable physical bonds are selected from conventional such bonds, including but not limited to, hydrogen bonds, electrostatic bonds, host-guest bonds including αCyclodextrin(CD) as a host and n-butyl (n-Bu), Adamantyl, Benzyl, Trans-Azobenzene groups as a guest; βCD as a host and Adamantyl, t-butyl, Cyclohexyl(ester), Cyclododecyl(amide), Benzyl, 2-Naphthylmethyl, 1-Pyrenylmethyl, Ferrocene, Trans-Azobenzene groups as a guest; γCD as a host and Cyclododecyl, Benzyl, 2-Naphthylmethyl, 9-Phenanthrylmethyl, 1-Pyrenylmethyl groups as a guest) (e.g., see FIG. 2). The cleavable covalent bonds may also be selected from conventional such bonds, including but not limited to, boron-oxygen bonds including boronic acid-diol, phenylboronate ester, disulfide bonds, Hydrazone bonds, Imine bonds, Diels-Alder bonds, Carbon-carbon/carbon-sulfur bonds including Trithiocarbonate (TTC) and thiuramdisulfide (TDS), Oxime bonds (e.g., see FIG. 2).

According to embodiments of the present invention, the (iv) one or more crosslinkers are selected from conventional crosslinkers, including but not limited to gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate), and combinations thereof. Because the present adhesive material can be used in a wide variety of biomedical applications, the crosslinkers used in the present invention are preferably biocompatible (although for non-biomedical applications it would not be necessary to utilize only biocompatible crosslinkers).

According to a preferred embodiment, an adhesive material comprises: (i) about 5 w/w % to about 50 w/w % of one or more hydrophilic polymers, (ii) about 1 w/w % to about 10 w/w % of one or more amine coupling groups grafted via (iii) cleavable physical and/or covalent bonds, and (iv) and about 0.05 w/w % to about 0.15 w/w % of one or more crosslinkers, and deionized water for the remaining parts in its as-prepared (before drying) form.

According to a specific embodiment of the present invention, the adhesive material is a bioadhesive material formed of interpenetrating networks of (i) polyvinyl alcohol (PVA) and poly(acrylic acid) (PAA) grafted with (ii) N-hydroxysuccinimide (NHS) ester via (iii) cleavable disulfide bonds in the dry state. The instant adhesion of the adhesive material relies on the removal of interfacial water and/or other physiological fluids (e.g., saline, interstitial fluid, intracellular fluid, etc.) from the wet surface(s) (particularly wet tissue surfaces) by the highly hygroscopic PAA network in the bioadhesive (e.g., see FIG. 4A), which simultaneously forms instant physical crosslinking such as hydrogen bonds and electrostatic interactions to the surface(s). Subsequent covalent crosslinking of the cleavable NHS ester in the bioadhesive material with primary amine groups on the tissue surface further improves the long-term adhesion stability and strength (FIG. 4A).

According to a preferred embodiment, the adhesive material is a poly(vinyl alcohol) (PVA)-based adhesive material. A PVA-based adhesive material according to an embodiment of the present invention preferably includes: about 20 w/w % to about 40 w/w %, more preferably about 25 w/w % to about 35 w/w %, and even more preferably about 30 w/w % polyacrylic acid; about 5 w/w % to about 15 w/w %, more preferably about 10 w/w % PVA; about 0.5 w/w % to about 1.5 w/w % PAAc-disulfide-NHS ester, more preferably about 1 w/w % PAAc-disulfide-NHS ester; about 0.01 w/w % to about 0.1 w/w % poly(ethylene glycol methacrylate) (PEGDMA), more preferably about 0.05 w/w % PEGDMA; and deionized water for the remaining parts, in its as-prepared (before drying) form.

According to an exemplary embodiment, a gelatin-based adhesive comprises about 35 w/w % polyacrylic acid, about 10 w/w % PVA, about 1 w/w % PAAc-disulfide-NHS ester, about 0.05 w/w % PEGDMA, and deionized water for the remaining parts in its as-prepared (before drying) form.

According to embodiments of the present invention, the adhesive material has a top surface and a bottom surface. Preferably, the adhesive material is generally in the form of a sheet, tape, or film (all of which may be perforated, partially perforated, or not perforated), with a top surface and a bottom surface. In preferred embodiments, the adhesive material is provided with a removable backing layer or an integrated (non-removable) material layer disposed upon one or more adhesive surfaces. For example, one or more removable backing material layers may be disposed upon one or more adhesive surfaces, particularly to aid in handling the adhesive material and to provide protection against moisture. If desired, one or more integrated material layers may be disposed upon one or more adhesive surfaces, particularly to provide one or more non-adhesive sides or portions of sides for single-sided usage or for partial side usage.

For example, an entire top surface of an adhesive material may have a removable backing layer disposed thereon, while the entire bottom surface may have an integrated material layer disposed thereon. As such, only the adhesive properties of the top surface of the adhesive material may be used in an application by removing the backing layer prior to use. Similarly, both the entire top and bottom surfaces may have a removable backing layers disposed thereon, such that the adhesive properties of both the top and bottom surfaces of the adhesive material may be used in an application by removing the backing layers prior to use. In some applications, it may be desirable to have a combination of one or more removable backing layers disposed on a single surface (e.g., a top surface) and one or more integrated material layers also disposed on that same single surface (e.g., top surface) so that the adhesive properties of only those portions of the surface (e.g., top surface) with the removable backing layer disposed thereon may be used by removing the backing layer from those portions, while the adhesive properties of those portions of the surface (e.g., top surface) with the integrated backing material layer disposed thereon are not utilized. For example, a central portion of a top surface of an adhesive material may have an integrated material layer disposed thereon, while portions of the top surface surrounding the central portion may have one or more removable backing layers disposed thereon. This will provide a configuration in which the top surface of the adhesive material will adhere to a wet surface along an outside portion or perimeter of the adhesive material upon removal of the removable backing layers, while a central portion of the adhesive material will not adhere due to the integrated material layer which is not removed.

The integrated material layer or removable backing layer is provided so as to prevent adhesion of the material prior to the intended time of use. As such, the removable backing layer or integrated material layer is one which blocks the adhesive properties of the material. The integrated material layer or removable backing layer is provided so as to prevent adhesion of the material to non-targeted tissues during and after application on wet tissues. As such, the integrated material layer or removable backing layer is one which is non-adhesive to wet biological tissues. The removable backing layer or integrated material layer may be disposed directly on (i.e., without anything disposed between) the one or more surfaces of the adhesive material. In some embodiments, a layer or glue or other substance used for sticking materials together is disposed in between the one or more surfaces of adhesive material and the integrated material layer or removable backing layer. The removable backing layer or integrated material layer can be fabricated of any substance which prevents adhesion of the adhesive material to a wet surface. The integrated material layer or removable backing layer can be fabricated of any substance which is non-adhesive to wet biological tissues. In particular, as described herein, the adhesive material is in the form of a dry material that absorbs liquid from a wet surface when placed into contact with the wet surface, which causes the dry material to swell. This absorption of liquid and swelling of the dry adhesive material provides instant temporary crosslinking between the adhesive material and the wet surface, and further allows for fast subsequent covalent coupling or crosslinking between the adhesive material and the wet surface. As such, the removable backing layer or integrated material layer can generally be fabricated of any material that prevents liquid from coming into contact with the surface of the adhesive material. As such, the integrated material layer or backing material layer can generally be fabricated of any material that does not form an adhesive interface with wet biological tissues. Due to the use of the adhesive materials of the invention, the removable backing layer or integrated material layer should be fabricated of a biocompatible material. According to embodiments of the invention, the removable backing layer is fabricated of polyethylene or any hydrophobic polymer-coated paper and poly(methyl methacrylate) or any hydrophobic polymer films. Such removable backing layers can be adhered directly to the one or more surfaces of the adhesive material or can be adhered with a layer of glue or other adhesive such as acrylic adhesives. According to embodiments of the invention, the integrated material layer is fabricated of silicone elastomer, thermoplastic polyurethane, hydrogel, or any other biocompatible materials without adhesiveness to wet tissues. Such integrated material layers can be adhered directly to the one or more surfaces of the adhesive material.

According to an embodiment of the present invention, the adhesive material is in the form of a dry film or tape that can be applied directly on a surface of interest (e.g., after removing a removable material layer or backing material layer provided on one or more surfaces of the adhesive material without any other preparation steps). For example, in wet physiological environments, biological tissues are commonly covered with a thin layer of water. Upon the application of the present invention adhesive material, this water or fluid becomes interfacial fluid between the tissues and the applied adhesive, which commonly impedes the formation of rapid and robust adhesion between the tissues and the adhesive. To achieve instant tough adhesion on wet tissues, the present invention adhesive adopts a dry-crosslinking mechanism to remove the interfacial fluid and form adhesion on wet tissues (e.g., as depicted in FIG. 4A). For example, the (i) one or more hydrophilic polymers or copolymers (e.g., PVA and PAA networks) of the dry adhesive material can absorb the interfacial fluid to dry the wet tissue surfaces under gentle pressure (e.g., 1 kPa) applied for seconds (preferably less than 5 seconds). Simultaneously, the PAA network (or other suitable hydrophilic polymer/copolymer network) of the adhesive material provides abundant groups (e.g., carboxylic acid groups) that can form instant physical crosslinks (i.e. hydrogen bonds) with the tissue surface (see FIGS. 4A and 5). Furthermore, the cleavable amine (e.g., NHS ester) groups grafted to the PAA network (or other suitable hydrophilic polymer/copolymer network) forms stable covalent crosslinks (i.e. amide bonds) with primary amine groups abundant on the tissue surface within a few minutes (e.g., see FIGS. 4A and 5). After adhering to the tissue surface(s), the swollen bioadhesive becomes a thin layer of hydrogel having a stretchability of at least 7 times and fracture toughness on the order of 1,000 J m$^{-2}$ and higher.

Figure 5:
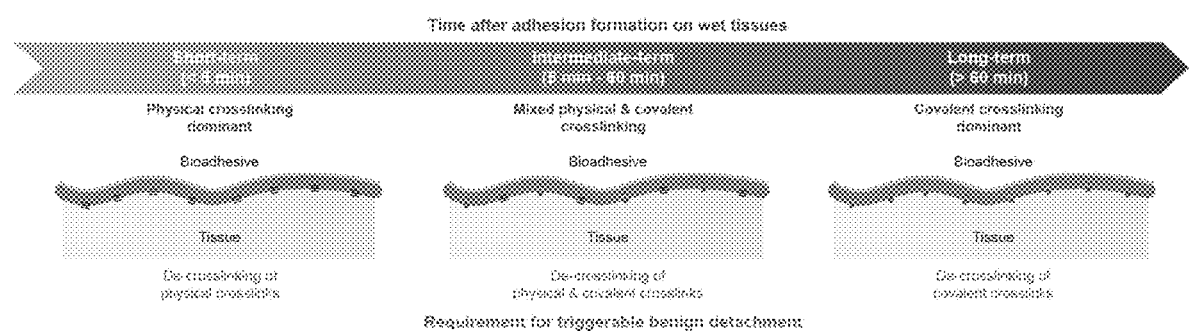
FIG. 5 schematically illustrates different timescales of adhesion and the corresponding requirement for triggerable detachment of the bioadhesive material according to an embodiment of the present invention.

According to the present invention, the tough adhesion between the adhesive material and the desired surface (e.g., wet tissue surface) relies on both physical and covalent crosslinks whose relative contributions vary at different timescales of adhesion. In the short term (<5 min), the instant physical crosslinks (i.e. hydrogen bonds) dominate the adhesion between the adhesive material and the surface. The contribution of the physical crosslinks to the adhesion decreases over time, as the equilibration and subsequent neutralization of carboxylic acid groups in the adhesive material deprives the adhesive's ability to form physical crosslinks with the tissue surface (e.g., as depicted in FIGS. 4B and 5). Therefore, the contribution of the covalent crosslinks (i.e. amide bonds) to the adhesion gradually increases in the longer term (FIG. 5).

The timing in which the present invention adhesive needs to be detached from a surface can vary from immediately after application (for example, in a situation where the adhesive must be repositioned because it was initially misplaced), to within minutes after application, to hours after application (for example, for intraoperative removal of temporary adhesives applied for subsequent definitive surgical repair), or even days to weeks after application (for example, in the case of removal of implanted devices which were implanted using the adhesive material). Therefore, the present invention provides an adhesive material having a triggerable detachment mechanism, wherein the triggerable detachment mechanism is biocompatible and effective across a broad timeframe.

Figure 4C:
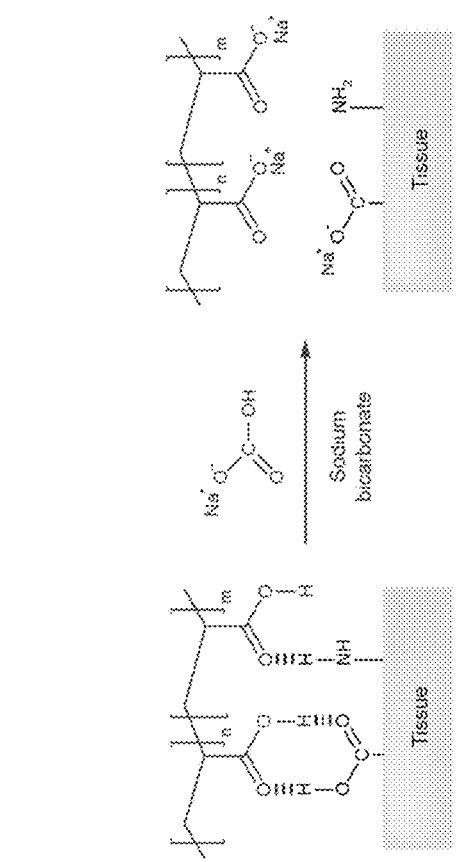
Figure 6:
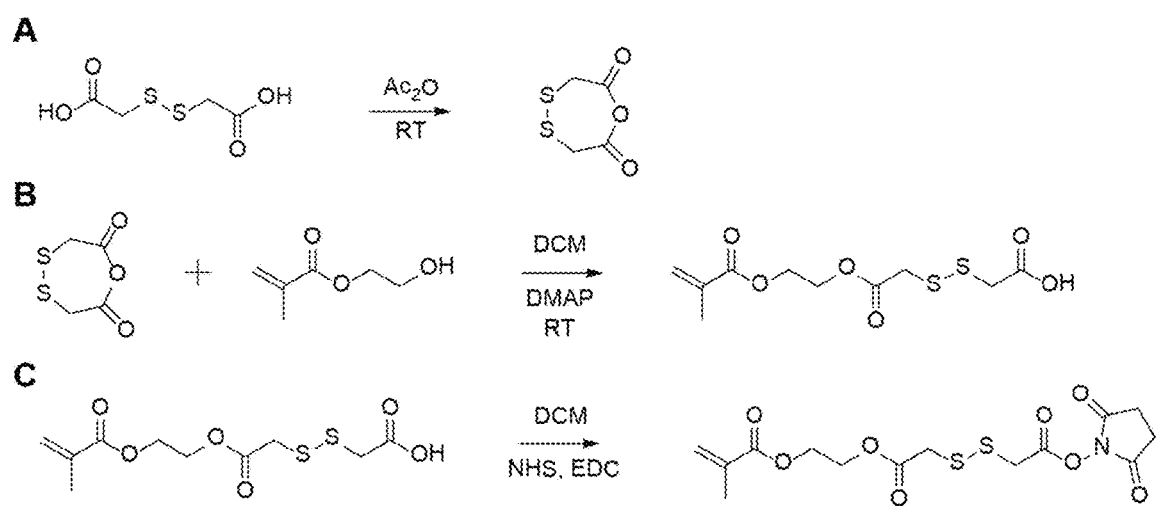
FIGS. 6A-C illustrate chemical schemes for the synthesis of functional monomer according to embodiments of the present invention.

According to the present invention, the adhesive material is provided with both physical and covalent crosslinks that are cleavable on-demand by a biocompatible triggering solution (FIG. 4A). In particular, the physical crosslinks are cleavable through pH-dependent de-crosslinking, particularly through cleaving the physical crosslinks of hydrogen bonds. Sodium bicarbonate (SBC) is an example of a triggering agent that can be used to provide cleaving through pH-dependent de-crosslinking (e.g., FIG. 4B). To provide the adhesive material with cleavable covalent crosslinks, cleavable disulfide bonds are introduced between the NHS ester groups (amine groups) and the one or more hydrophilic polymers or copolymers (e.g., PAA network) by synthesizing a novel functional monomer (e.g., see FIGS. 6 and 7). As such, in order to cleave these covalent crosslinks, a biocompatible reducing agent such as glutathione (GSH) is used as a triggering agent. Contacting an adhesive that has adhered to a surface via cleavable covalent bonds with such a triggering agent results in the pendant thiol group in the trigger (e.g., GSH) breaking the disulfide bonds in the bioadhesive into thiol groups, thus cleaving the covalent crosslinks between the bioadhesive and the tissue surface (FIG. 4C). Beneficially, the present invention adhesive material and associated cleaving mechanism by which both physical and covalent bonds are broken can be achieved under physiological conditions.

The high processability of the present invention adhesive material further allows for flexible fabrication into diverse shapes such as, but not limited to, flat sheets, perforated sheets, and tape-like rolls to meet various needs. The adhesive material also possesses several favorable properties for biological applications. In particular, the adhesive material in swollen state exhibits a low shear modulus of about 20 kPa and stretchability on the order of 7 times of its original unswollen length, thus being comparable to soft tissue properties. The dry adhesive material can also be fabricated to be highly biocompatible and biodegradable, owing to its composition.

Figure 7:
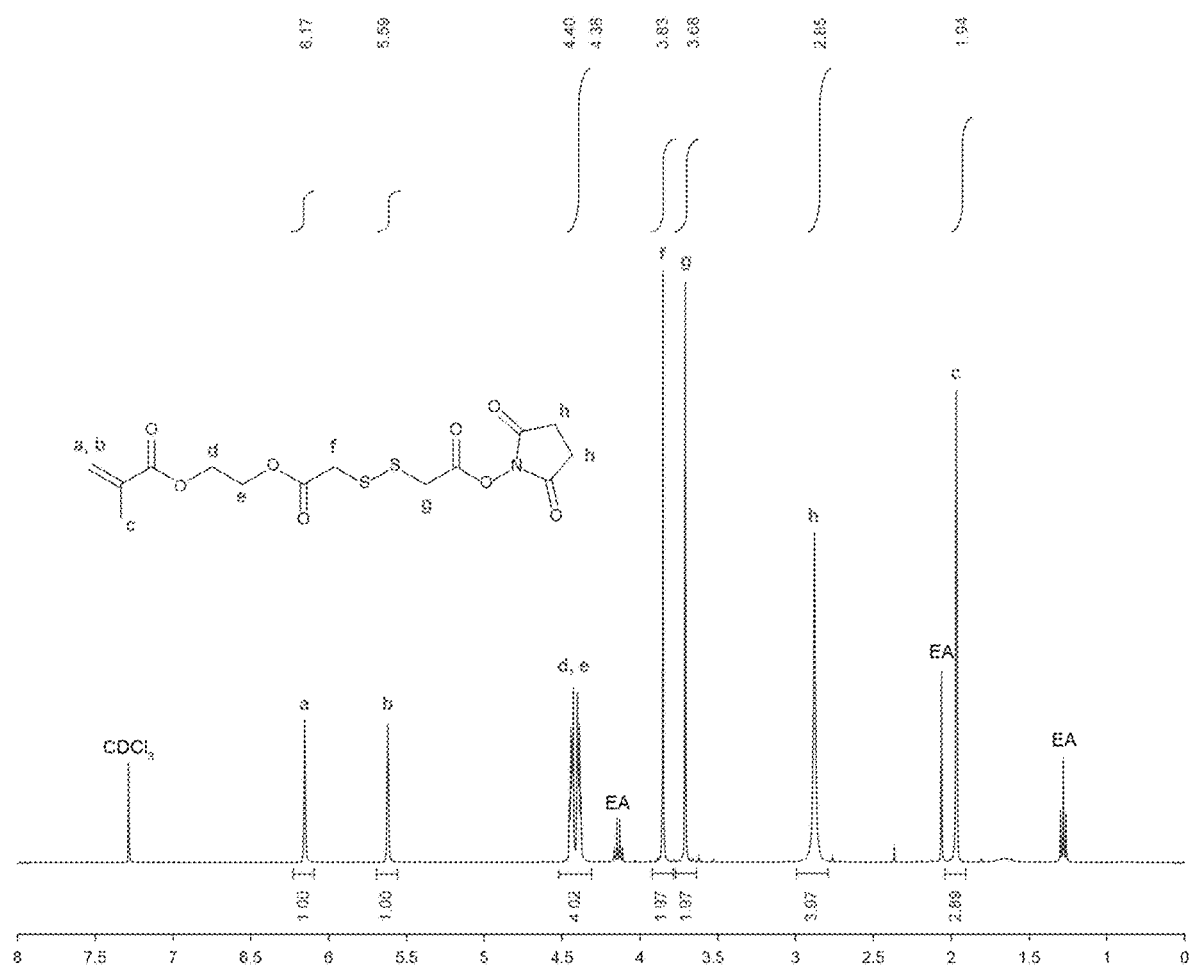
FIG. 7 graphically depicts $^1$H NMR spectra for synthesized NHS ester functionalized monomer with a disulfide bond according to an embodiment of the present invention.
Figure 8:
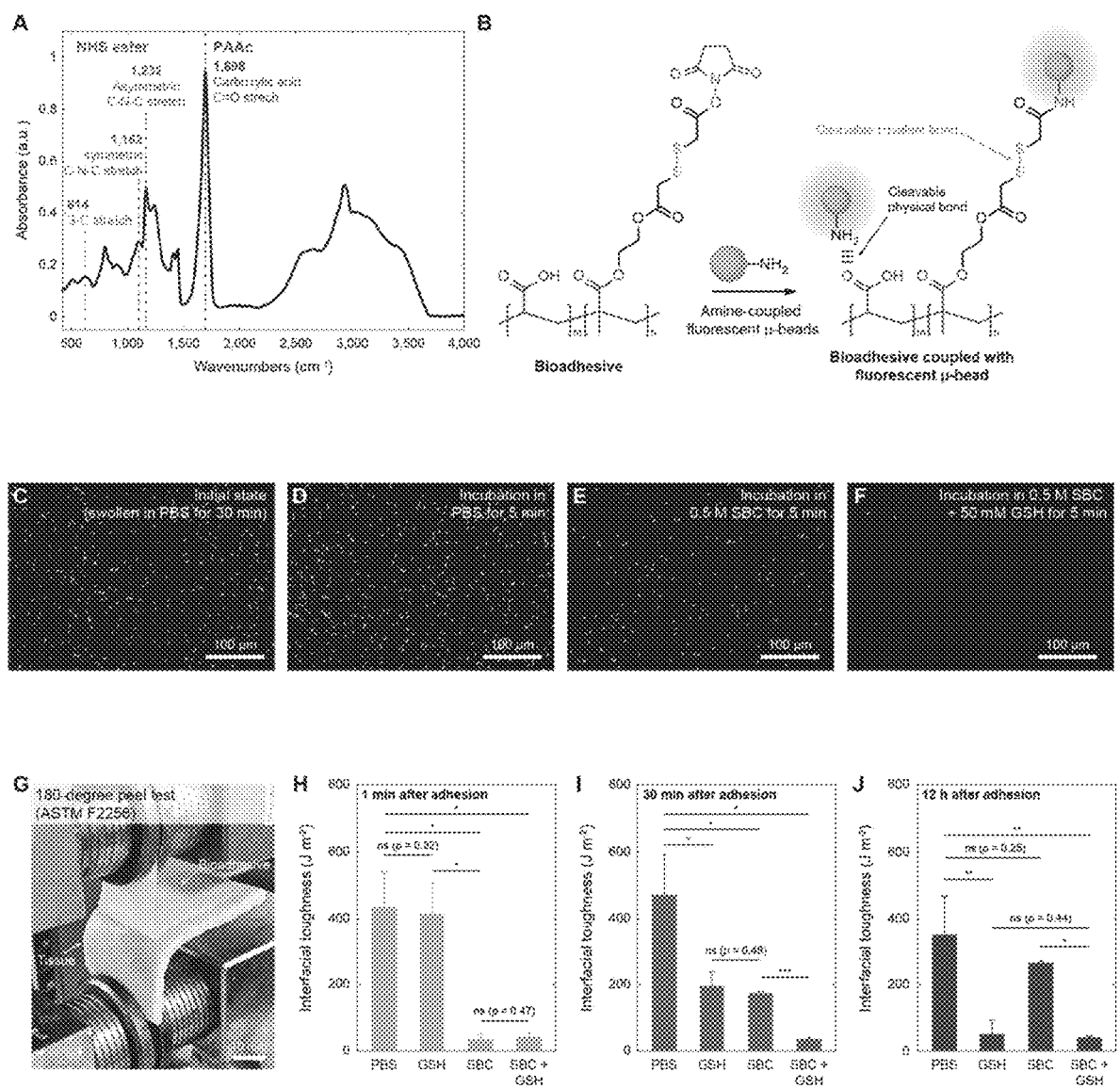
FIGS. 8A-J illustrate triggerable detachment of a bioadhesive material according to an embodiment of the present invention, with FIG. 8A graphically depicting the FTIR spectra of the bioadhesive with associated peaks for carboxylic acid (1,698 cm$^{-1}$), disulfide (614 cm$^{-1}$), and NHS ester (1,162 and 1,232 cm$^{-1}$) functional groups, FIG. 8B schematically illustrate validation of triggerable detachment based on fluorescent primary amine-coupled microbeads, FIGS. 8C-F showing fluorescent microscope images for the bioadhesive sample in the initial state (FIG. 8C), 5 min after incubation in PBS (FIG. 8D), PBS with 0.5 SBC (FIG. 8E), and PBS with 0.5 M SBC and 50 mM GSH (FIG. 8F), FIG. 8G showing photograph of 180-degree peel test setup for the measurement of interfacial toughness, and FIGS. 8H-J illustrating interfacial toughness between the bioadhesive and wet porcine skin tissues 5 min after applying various solutions in short-term (FIG. 8H), intermediate-term (FIG. 8I), and long-term (FIG. 8J) adhesion. Values in (FIGS. 8H-J) represent the mean and the standard deviation (n=4). P values are determined by a Student's t-test; ns, not significant (p>0.05); * p≤0.05;  p≤0.01; * p≤0.001. Scale bars are shown in images.
Figure 9:
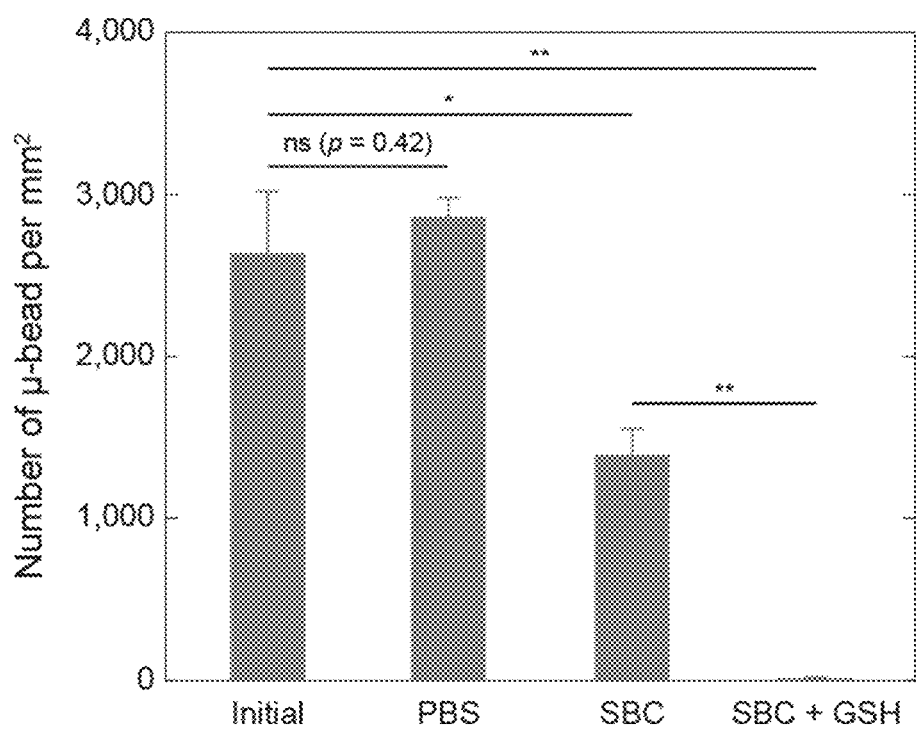
FIG. 9 graphically depicts the number of adhered fluorescent microbeads on a bioadhesive according to an embodiment of the present invention 5 min after incubation in varying solutions depicted in FIGS. 3C-F. Values represent the mean and the standard deviation (n=4). P values are determined by a Student's t-test; ns, not significant (p>0.05); * p≤0.05; ** p≤0.01.

In order to evaluate the adhesion and triggerable detachment performance of the present invention adhesive material, the attenuated total reflection Fourier transform infrared spectroscopy (ATR-FTIR) analysis was used. First, the incorporation of carboxylic acid (1,698 cm$^{-1}$), NHS ester (1,162 and 1,232 cm$^{-1}$), and disulfide (614 cm$^{-1}$) groups in the adhesive material was determined (see FIG. 8A). To validate the triggerable cleavage of the physical and covalent crosslinks of the adhesive, 0.5 M SBC and 50 mM GSH in PBS were used as triggering solutions. Primary amine-coupled fluorescent microbeads were used as a model to evaluate the adhesion and detachment between the adhesive and the amine-rich surfaces of the microbeads (FIG. 8B). A fluorescent microscope image of the bioadhesive incubated in PBS with the amine-coupled fluorescent microbeads for 30 min shows stably adhered microbeads on the present invention adhesive, owing to the physical and covalent crosslinks between the adhesive and the microbeads' surfaces (see FIGS. 7C and 8). The bioadhesive with the fluorescent microparticles was incubated in PBS alone, PBS with 0.5 M SBC, and PBS with 0.5 M SBC and 50 mM GSH for 5 min, respectively. The bioadhesive incubated in PBS alone exhibited no significant change in the number of adhered fluorescent microbeads (FIGS. 8D and 9). The bioadhesive incubated in PBS with 0.5 M SBC shows a significant reduction in the number of adhered fluorescent microbeads, although a substantial portion of the microbeads remains adhered (FIGS. 8E and 9). In contrast, the bioadhesive incubated in PBS with 0.5 M SBC and 50 mM GSH exhibit nearly complete detachment of the adhered fluorescent microbeads (FIGS. 8F and 9). These results demonstrate that the adhesion of the microbeads' amine-rich surfaces on the adhesive is stable under physiological conditions and that their complete triggered detachment requires the cleavage of both physical crosslinks (by SBC) and covalent crosslinks (by GSH).

Figure 10:
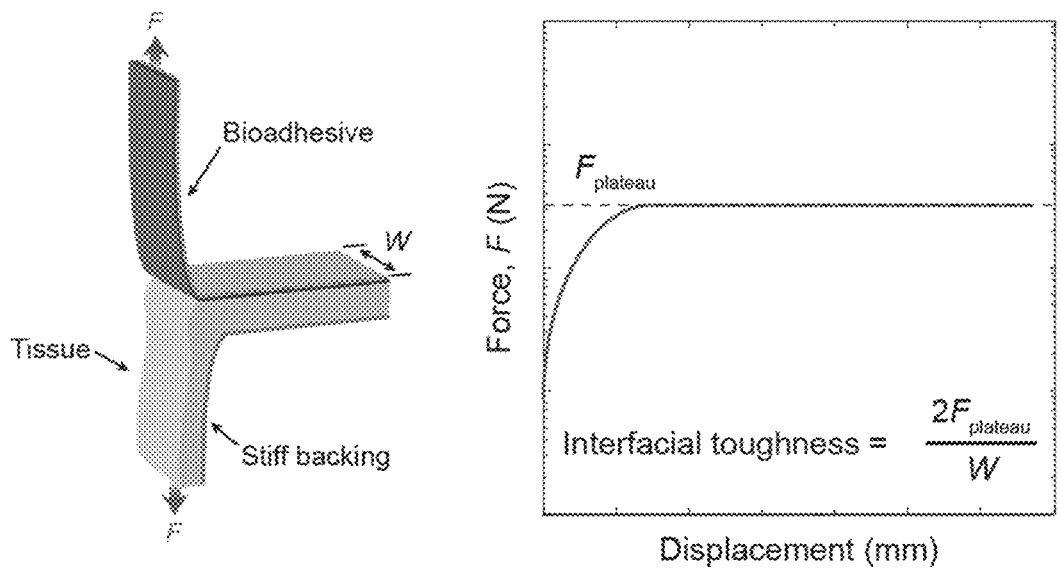
FIG. 10 schematically illustrates mechanical testing setups for interfacial toughness measurements based on the standard 180-degree peel test (ASTM F2256).
Figure 11:
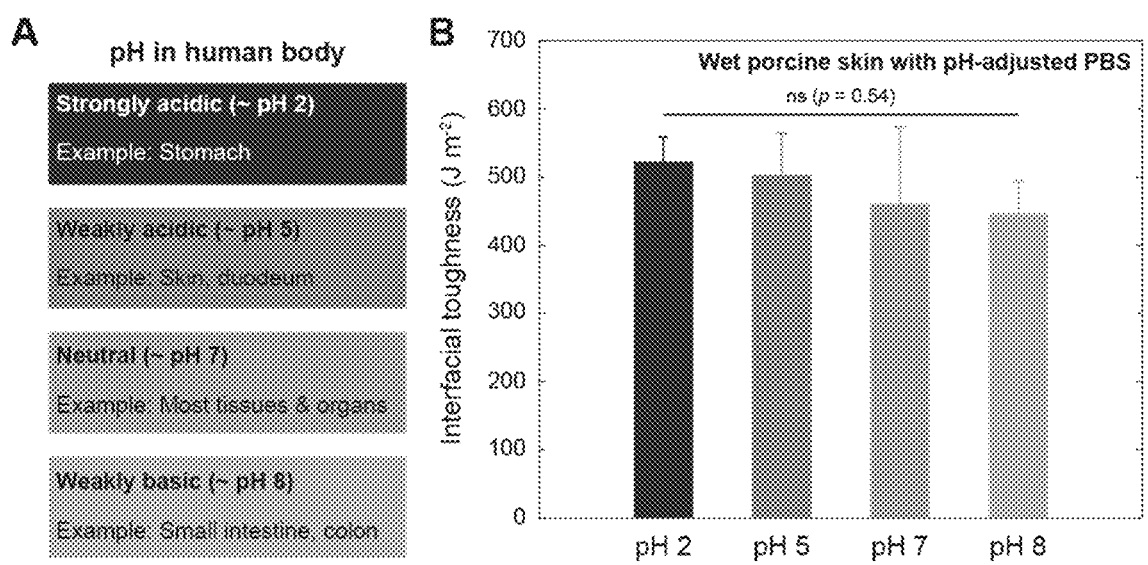
FIGS. 11A-B schematically illustrates the effect of pH on the adhesion performance of a bioadhesive according to an embodiment of the present invention, with FIG. 11A showing various pH values in a human body, and FIG. 11B illustrating interfacial toughness between the bioadhesive and wet porcine skin tissues incubated in various pH-adjusted PBS. Values in FIG. 11B represent the mean and the standard deviation (n=3). P values are determined by one-way ANOVA and Tukey's multiple comparison test; ns, not significant (p>0.05).

In addition, the effect of the present invention triggerable detachment mechanism on adhesion performance was analyzed. In this analysis, the interfacial toughness between the adhesive material and wet porcine skin tissues was measured following the standard test for tissue adhesives (180-degree peel test, ASTM F2256) (FIGS. 8G and 10). As shown in FIG. 8H-J, the present invention adhesive material forms tough adhesion with interfacial toughness over 400 J m$^{-2}$ on wet porcine skin tissues upon contact and gentle pressure (e.g., 1 kPa) application for less than 5 seconds, demonstrating instant tough adhesion properties. Furthermore, the adhesive was demonstrated to form instant tough adhesion under various physiological pH conditions, potentially allowing its use in various locations in the human body (FIG. 11).

Figure 12:
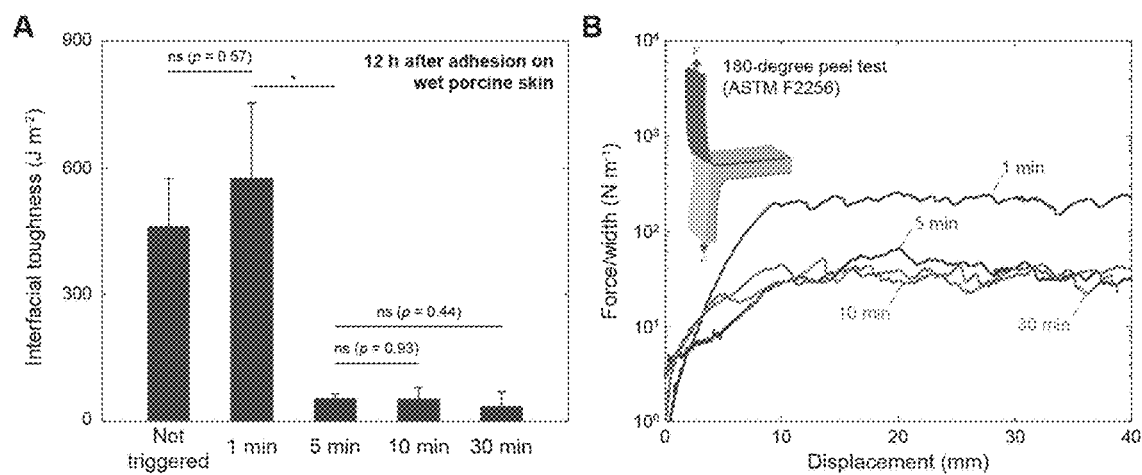
FIGS. 12A-B graphically depict the efficiency of the triggerable detachment of the bioadhesive according to an embodiment of the present invention, with FIG. 12A illustrating interfacial toughness between the bioadhesive and wet porcine skin tissues without triggering and 1, 5, 10, and 30 min after the application of a triggering solution, and FIG. 12B illustrating representative force/width vs. displacement curves for the 180-degree peel tests. Values in FIG. 12A represent the mean and the standard deviation (n=4). P values are determined by a Student's t-test; ns, not significant (p>0.05); * p≤0.05.
Figure 13:
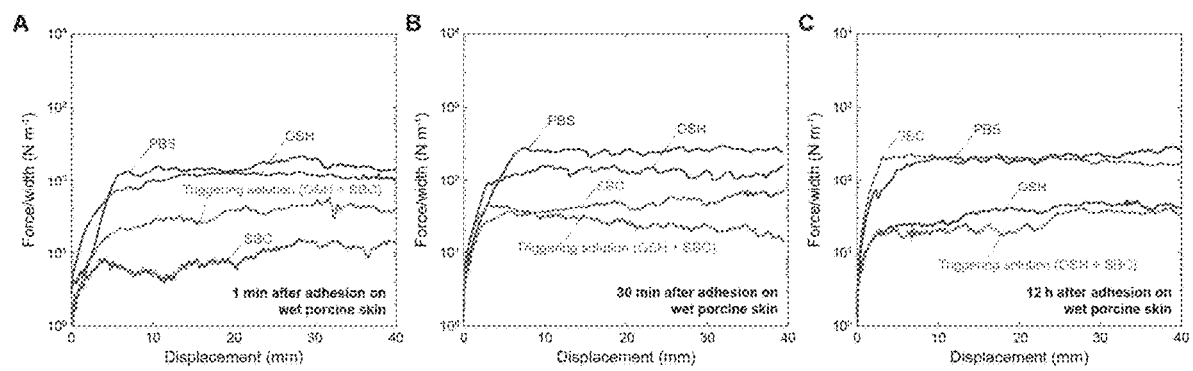
FIGS. 13A-C graphically illustrate representative force/width vs. displacement curves for the 180-degree peel tests of short-term (FIG. 13A), intermediate-term (FIG. 13B), and long-term (FIG. 13C) adhesion in FIGS. 3H-J.

In order to analyze triggerable detachment, the following were applied to the present invention adhesive which was adhered to porcine skin: PBS alone, PBS with 50 mM GSH, PBS with 0.5 M SBC, and PBS with 0.5 M SBC and 50 mM GSH. Thereafter, interfacial toughness was measured (FIGS. 12 and 13). For the short-term adhesion (triggering solutions applied 1 min after adhesion formation), the samples treated with the solutions containing SBC (PBS with 0.5 M SBC, PBS with 0.5 M SBC and 50 mM GSH) showed a significant reduction in the measured interfacial toughness, while the samples treated with the solution containing GSH alone (PBS with 50 mM GSH) exhibited negligible difference from the samples treated with PBS alone (FIG. 8H). This demonstrates that SBC and its capability to cleave the physical crosslinks play a critical role in the triggerable detachment of short-term adhesion (detachment a short time after adhesion, e.g., 1 min after adhesion). For the intermediate-term adhesion (here, where the triggering solutions were applied 30 min after adhesion formation), all other samples exhibited a substantial decrease in the measured interfacial toughness compared to the samples treated with PBS alone. Also, the samples treated with the solution containing both SBC and GSH (PBS with 0.5 M SBC and 50 mM GSH) demonstrated significantly lower interfacial toughness than the samples treated with the solution containing either SBC or GSH (PBS with 50 mM GSH or PBS with 0.5 M SBC) (FIG. 7I). This demonstrates that both SBC and GSH and their capability to cleave the physical crosslinks and the covalent crosslinks play a critical role in the triggerable detachment of the adhesive after intermediate-term adhesion. For the long-term adhesion (solutions applied 12 hours after adhesion formation), the samples treated with the solutions containing GSH (PBS with 50 mM GSH and PBS with 0.5 M SBC and 50 mM GSH) show significantly lower interfacial toughness than other samples. Also, the samples treated with the solution containing SBC alone (PBS with 0.5 M SBC) exhibit negligible difference from the samples treated with PBS alone (FIG. 8J). This demonstrates that GSH and its capability to cleave the covalent crosslinks play a critical role in triggerable detachment of the long-term adhesion. These results validate that the triggering solution of PBS with 0.5 M SBC and 50 mM GSH can cleave both physical crosslinks (by SBC) and covalent crosslinks (by GSH) and substantially decrease the interfacial toughness across a broad timeframe after the formation of adhesion (FIGS. 4 and 5).

Figure 14:
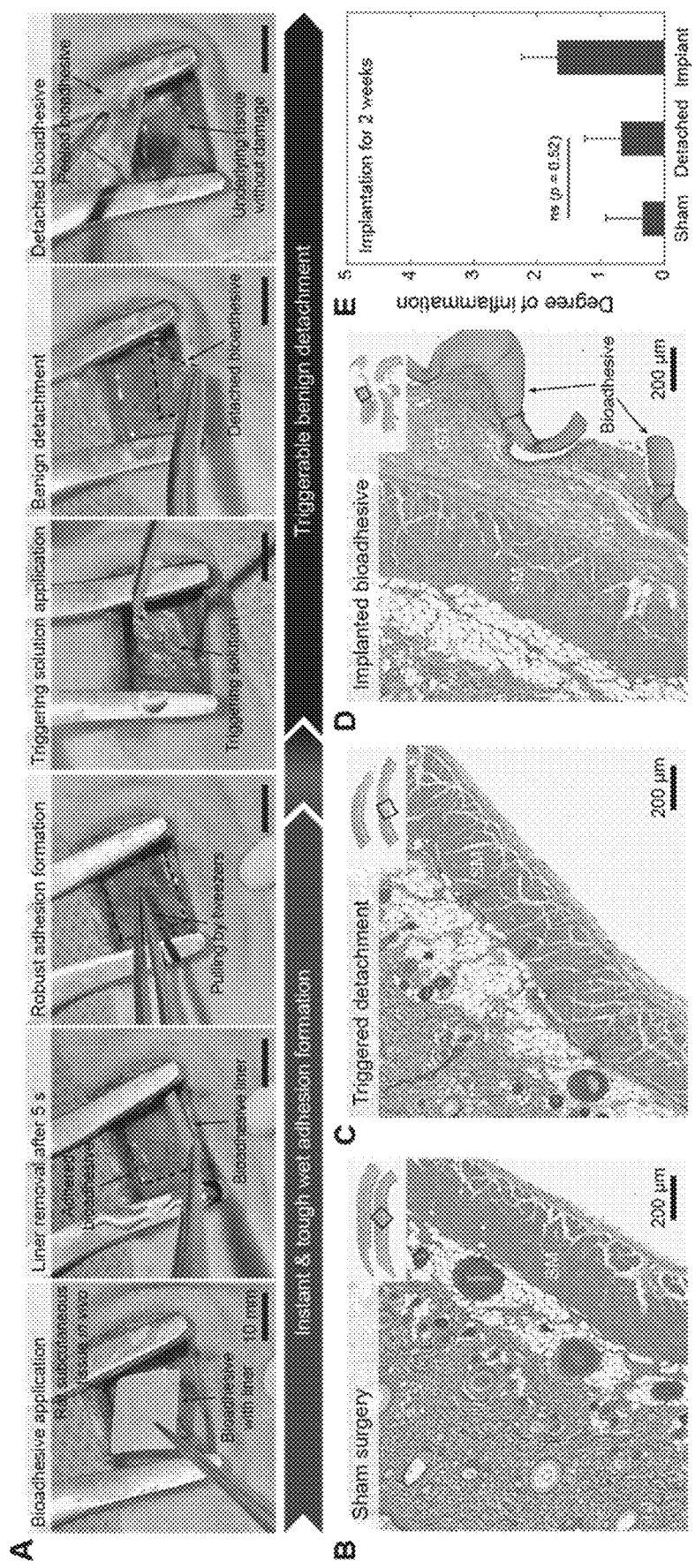
FIGS. 14A-E illustrate in vivo applicability and biocompatibility of the bioadhesive according to embodiments of the present invention, with FIG. 14A illustrating photographs for instant robust adhesion and triggerable detachment of the bioadhesive in rat subcutaneous space in vivo, FIGS. 14B-D illustrating representative histological images stained with H&E for biocompatibility assessment of the sham surgery (FIG. 14B), the triggered detachment of the bioadhesive (FIG. 14C), and the implanted bioadhesive (FIG. 14D), and FIG. 14E illustrating the degree of inflammation of the sham surgery, the triggered detachment of the bioadhesive, and the implanted bioadhesive groups evaluated by a blinded pathologist (0, normal; 1, very mild; 2, mild; 3, moderate; 4, severe; 5, very severe) after 2 weeks of subcutaneous implantation. SM and GT indicate skeletal muscle and granulation tissue, respectively. All experiments were repeated four times with similar results. Values in FIG. 14E represent the mean and the standard deviation (n=4). P values are determined by a Student's t-test; ns, not significant (p>0.05). Scale bars are shown in images.

To evaluate the adhesive material's capability of forming rapid, robust, and triggerable detachable adhesion to wet tissues in vivo, an adhesive patch according to the present invention was adhered to a muscular layer of a rat subcutaneous space followed by a triggered detachment of the bioadhesive on-demand (FIG. 14A). It was demonstrated that the adhesive patch adhered to the muscular layer of the rat after gently pressing for 5 sec, forming adhesion robust enough to resist pulling apart by tweezers. To detach the adhered adhesive patch on-demand, a triggering solution was applied in the subcutaneous space of the rat for 5 min, which resulted in on-demand removal of the adhesive patch without observable damage to the underlying tissue surface (FIG. 14A). The in vivo biocompatibility of the adhesive and the triggerable detachment process was further evaluated in a rat dorsal model of subcutaneous implantation (FIG. 14B-E). The histological assessment made by a blinded pathologist indicated that the triggering solution and the triggerable detachment process generated a mild inflammatory reaction comparable to that generated by a sham control group (surgery without implantation) at 2 weeks after the surgeries (FIGS. 14B,C and E). Furthermore, the histological assessment of the bioadhesive implanted for 2 weeks showed a mild to moderate inflammatory reaction (FIG. 14D,E). These results demonstrate the biocompatibility of the present invention adhesive material and its triggerable detachment.

Triggerable and atraumatic on-demand detachment of bioadhesives can find potential applications in various clinical scenarios in different timeframes. In the short timeframe, the bioadhesives can accidentally be applied incorrectly on a tissue surface, which requires the immediate correction for successful surgical treatment. In such clinical scenarios, the triggerable detachment provided by the present invention adhesive material allows for prompt revision of an incorrectly applied adhesive without causing damage to the underlying tissue. In the intermediate timeframe, emergency treatments of clinically unstable patients frequently require an initial surgery (e.g., providing temporary organ sealing for initial damage control surgeries, where the temporary organ sealing may require temporary adhesion for hours) followed by a subsequent definitive surgical repair. In such clinical scenarios, the triggerable detachment of the present invention adhesive can allow on-demand removal of the adhesive applied during the initial surgery for subsequent definitive surgical repair. In the long timeframe, various medical devices such as cannulae and drains in cardiac surgeries and drug depots in localized cancer chemotherapies require subsequent removal after several days to weeks of implantation. In such clinical scenarios, the present invention adhesive material can provide both secure fixations as well as atraumatic retrieval of the devices through the provided triggerable detachment properties and mechanism.

Figure 15:
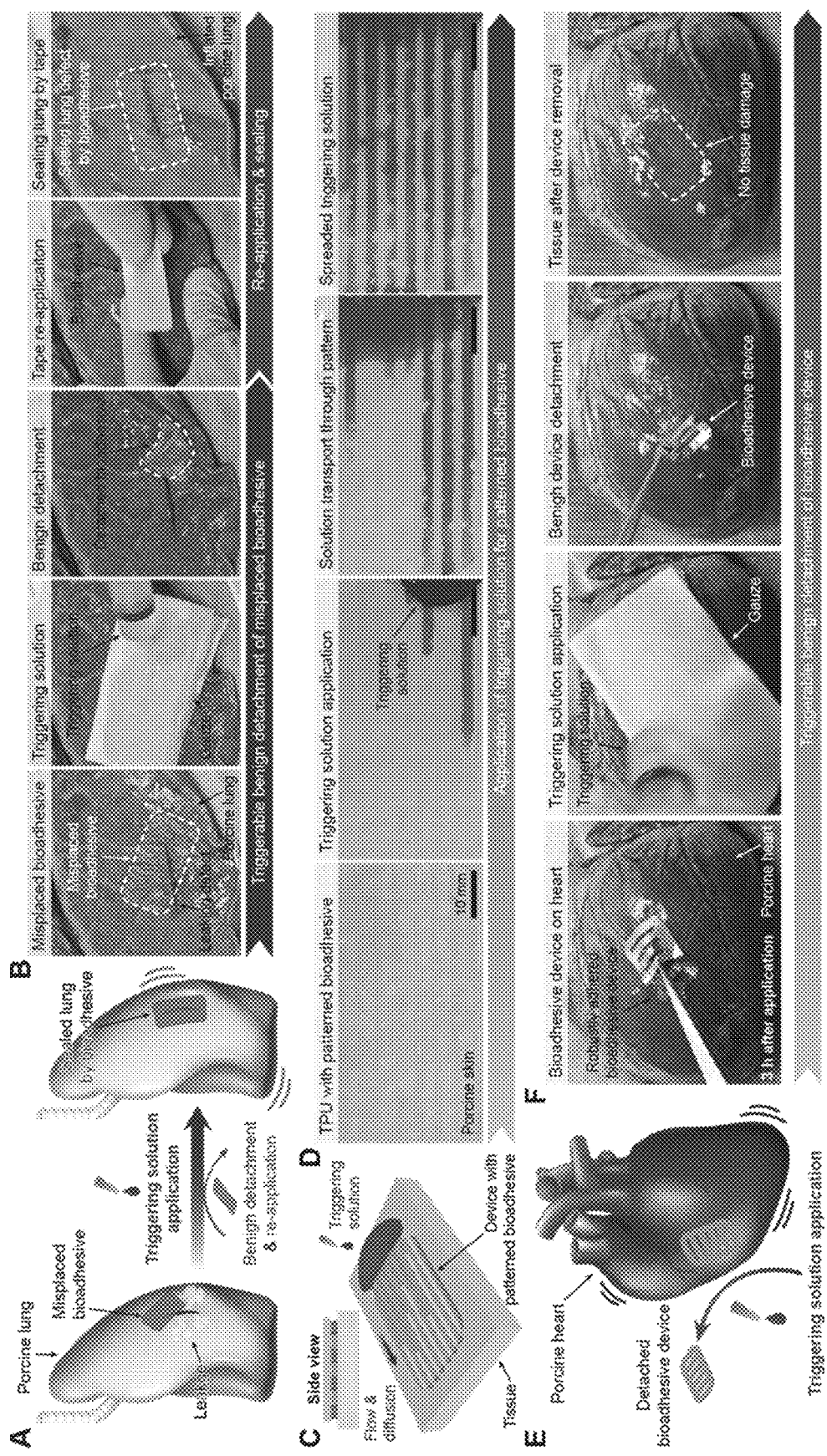
FIGS. 15A-F illustrate potential applications of bioadhesive materials according to embodiments of the present invention, with FIGS. 15A-B schematically illustrating (FIG. 15A) and photographically illustrating (FIG. 15B) correction of a misplaced bioadhesive and instant sealing of a lacerated ex vivo porcine lung by the bioadhesive material, FIGS. 15C-D schematically illustrating (FIG. 15C) and photographically illustrating (FIG. 15D) a patterned bioadhesive material for facile transport and diffusion of triggering solution for impermeable devices, and FIGS. 15E-F schematically illustrating (FIG. 15E) and photographically illustrating (FIG. 15F) instant robust adhesion and on-demand removal of a bioadhesive material on a beating ex vivo porcine heart.
Figure 16:
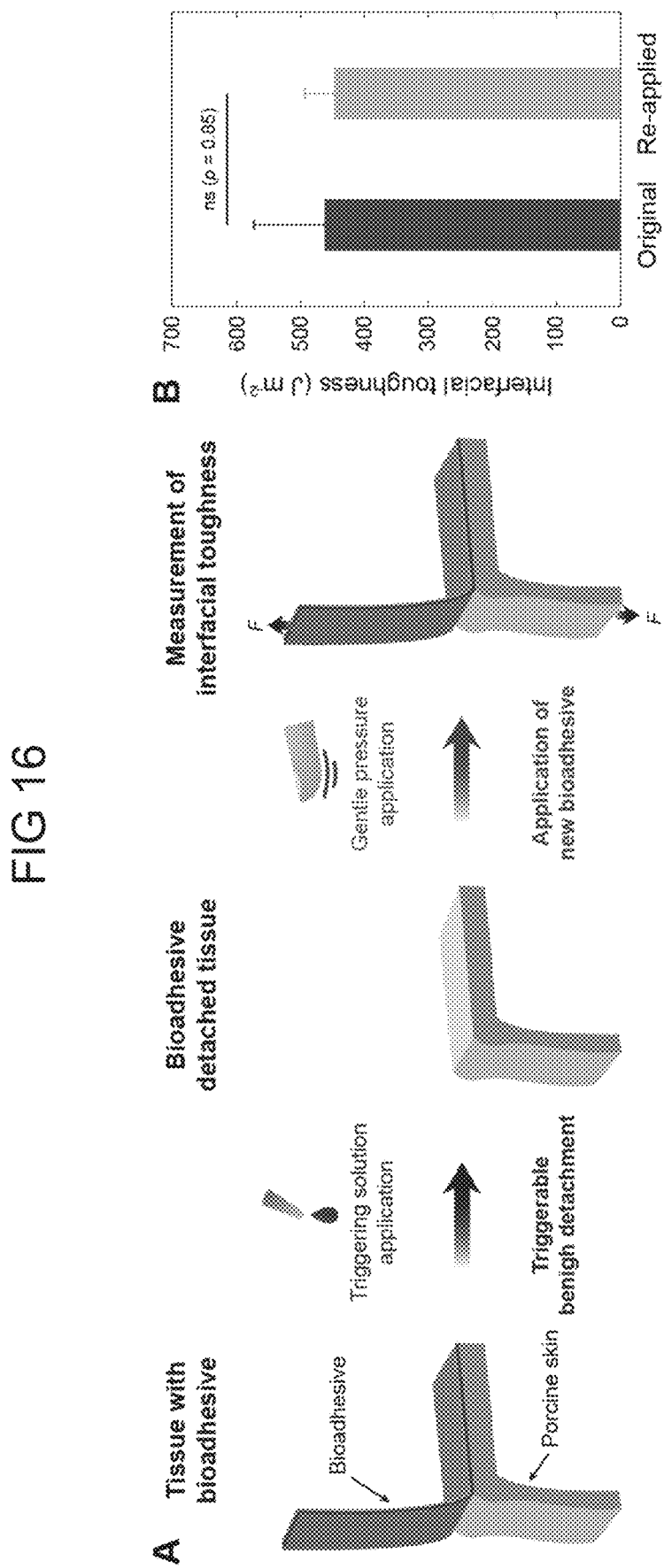
FIGS. 16A-B schematically and graphically illustrate the effect of triggerable detachment and re-application of a bioadhesive on the adhesion performance according to embodiments of the present invention where FIG. 16A show schematic illustrations for triggerable detachment and re-application of the bioadhesive material and FIG. 16B illustrate interfacial toughness between wet porcine skin tissues and the bioadhesive material originally applied and re-applied on the same tissue after triggerable detachment. Values in (FIG. 16B) represent the mean and the standard deviation (n=3). P values are determined by a Student's t-test; ns, not significant (p>0.05).

To investigate potential applications of the present invention detachable adhesive material, ex vivo proof-of-principle applications were provided on porcine organs. To demonstrate potential advantages of the instant tough adhesion and triggerable detachment of the present invention adhesive material in such situations, the successful repositioning of the adhesive that initially only incompletely sealed a lacerated porcine lung (3 cm incision) was demonstrated (FIG. 15A). As shown in FIG. 15B, the incorrectly adhered adhesive material was easily removed within 5 min after applying the triggering solution. Importantly, subsequent application of a new adhesive yielded the rapid formation of air-tight sealing of the porcine lung without compromising the adhesion performance (FIG. 16).

In another example, instant robust integration and on-demand removal of adhesive devices according to the present invention on wet dynamic tissues were demonstrated. Since many devices are not readily permeable to the present invention triggering solution, a patterned bioadhesive was designed to facilitate the transport and diffusion of the triggering solution to the adhesion interface (FIG. 15C). As demonstrated in FIG. 15D, a patterned bioadhesive according to the present invention was provided on an impermeable thermoplastic polyurethane (TPU) film, which allowed facile transport and diffusion of the triggering solution (red-colored by a food dye) across the adhered device. A mock device consisting of a gold-coated polyimide and a patterned bioadhesive according to the present invention was further demonstrated to form rapid and robust adhesion onto a beating ex vivo porcine heart (by introducing pressurized air inputs to mimic heartbeats) and was removable on-demand (FIG. 15E). Owing to the instant tough adhesion capability of the present invention adhesive material, the bioadhesive device was able to form robust and stable adhesion on the beating porcine heart within 5 sec of application. Also, the application of the triggering solution allowed for atraumatic removal of the adhered device within 5 min (FIG. 15F). The present invention adhesive material's capability to form instant robust adhesion on wet dynamic tissues and detachability on demand may, thus, find particular advantages for integration and potential atraumatic removal of implantable devices.

In addition to providing this beneficial on-demand triggerable detachment mechanism, the present invention adhesive material further provides faster and superior adhesion performance compared to existing tissue adhesives including commercially available cyanoacrylate adhesives (e.g., Histoacryl Flex™, Dermabond™), albumin-based adhesives (e.g., Bioglue™), polyethylene glycol-based adhesives (e.g., CoSeal™, DuraSeal™), fibrin glues (e.g., Tisseel™) as well as nanoparticle solutions and UV-curable surgical glues. The present invention adhesive material is applicable for a wide range of wet tissues including skin, tendon, stomach, muscle, heart, and liver. As such, the adhesive may find particular utility in surgical repair or closure of wounds as a promising alternative to suturing or stapling. The quick and strong adhesion properties of the dry adhesive material are also highly desirable for attachments of various functional devices on dynamic and deformable tissues, thus allowing for instant tough adhesion between wet tissues and various engineering solids including hydrogel, silicon, titanium, polydimethylsiloxane (PDMS), polyimide, and polycarbonate, which are unachievable with existing tissue adhesives. In other words, the present dry adhesive material can be used to attach one or more various engineering solids to one or more wet tissue surfaces.

Thus, the present invention provides an improved tissue adhesive in the form of an adhesive material, preferably in the form of a dry film or tape, which may be in the form of a dry double sided film or tape for certain uses, based on a dry cross linking mechanism which provides quick strong adhesion on diverse wet tissues and devices. The dry-preservable and ready-to-use nature of the adhesive material provides ease in storage, distribution, and usage for extended periods of time (e.g., over two weeks) without losing performances. As such, the present invention adhesive material eliminates the difficulties in storing perishable liquids or wet gels as well as mixing of reagents right before each use, common in existing tissue adhesives. Furthermore, the preset adhesive material is a simple composition, having high flexibility in fabrication. As such, it can provide substantial economic advantages, potentially facilitating the fast and widespread dissemination and translation of the material. These new capabilities of the adhesive material, both in its superior adhesive properties to a variety of surfaces, including wet tissues, as well as its ability for on-demand removal without causing trauma to delicate tissues, address a set of long-lasting challenges in existing tissue adhesives and may offer new opportunities for future developments in tissue engineering, drug delivery, and bio-integrated devices. The dry crosslinking mechanism for wet adhesion may further inspire the design of future adhesives in wet and underwater environments.

Materials and Methods for Example Embodiment

Synthesis of NHS Ester Functionalized Monomer With Disulfide Bond

To prepare NHS ester functionalized monomer with disulfide bond, 2,2' disulfanediyldiacetic acid (1.8 g, 10.0 mmol), and acetic anhydride (8.0 mL) were added to a 100-mL round-bottomed flask equipped with a magnetic stirring bar. The mixture was stirred at room temperature for 3 hours to obtain a homogeneous solution (FIG. 6A). Then, the solvent was removed in vacuo to afford 1,4,5-oxadithiepane-2,7-dione as a light-yellow oil. The oil was directly transferred into the mixture of 2-hydroxyethyl methacrylate (1.9 g, 15.0 mmol), 4-dimethylaminopyridine (DMAP; 12.0 mg, 1.0 mmol), and 15 mL of anhydrous dichloromethane (DCM). The solution was stirred at room temperature overnight and then the reaction was finalized by adding 30 ml of saturated $NaHCO_3$ solution (FIG. 6B). Then, the mixture was acidified with 1 M HCl to pH=2.0 and extracted with DCM. The organic phase was dried over $Na_2SO_4$ and concentrated under reduced pressure. The crude product was purified by flash column chromatography on silica gel with a mixture of MeOH and DCM (v/v=1/20) as the eluent to afford 6-(2-(methacryloyloxy)ethoxy)hept-6-enoic acid. The 6-(2-(methacryloyloxy)ethoxy)hept-6-enoic acid (2.94 g 10.0 mmol) was then dissolved in 30 ml anhydrous DCM and stirred with N-hydroxysuccinimide (NETS; 1.15 g, 10 mmol) in an ice bath for 30 mins. Then 1-[3-(dimethylamino)propyl]-3-ethylcarbodiimide hydrochloride (EDC; 1.55 g, 10 mmol) in 20 ml DCM was added dropwise into the above mixture. The solution was stirred overnight under a nitrogen atmosphere at room temperature (FIG. 6C). The crude product was purified by flash column chromatography on silica gel with a mixture of petroleum ether and ethyl acetate (v/v=1/1) as the eluent to afford the product as a colorless liquid. $^1$H NMR (400 MHz, CDCl$_3$, δ): 6.17 (p, 1H, —CH2), 5.59 (q, 1H, —CH2), 4.44-4.33 (m, 4H, —OCH2CH2O—), 3.83-3.68 (d, 4H, —CH2SSCH2-), 2.85 (s, —CH2-CH2-) 1.94 (s, 3H, —CH3) (FIG. 7).

Preparation of the Bioadhesive

To prepare the bioadhesive, polyvinyl alcohol (PVA; Mw=146,000-186,000, 7 w/w %), acrylic acid (AAc; 35 w/w %), α-ketoglutaric acid (0.2 w/w %), and poly(ethylene glycol methacrylate) (PEGDMA; Mn=550, 0.05 w/w %) were dissolved in deionized water. Then, 100 mg functional monomer (NHS ester functionalized monomer with disulfide bond) was dissolved in 1 ml acetone and added to 10 ml of the above stock solution to get a precursor solution. The precursor solution was then poured on a glass mold with spacers (the thickness was 210 µm unless otherwise mentioned) and cured in ultraviolet light (UV) chamber (284 nm, 10 W power) for 30 min. As a non-adhesive layer, 10 w/w % thermoplastic polyurethane solution was spin-coated on the cured bioadhesive at 400 rpm for 30 s and dried completely. The prepared bioadhesives were sealed in plastic bags with desiccant (silica gel packets) and stored at −20° C. before use. To pattern the bioadhesive, a large sheet of bioadhesive was cut into various patterns using a laser cutter (Epilog). Weighing paper (VWR) was used as a removable liner for the bioadhesive.

Preparation of the Triggering Solution

To prepare the triggering solution, 0.5 M sodium bicarbonate (SBC) and L-glutathione reduced (GSH) were dissolved in PBS. The triggering solution was filtered by using a 0.2-µm sterile syringe filter before use. For validation of the triggerable detachment of the bioadhesive, the bioadhesive was incubated in PBS with primary amine-coupled fluorescent microbeads (FluoSpheres™, Thermo Fisher Scientific) for 30 min in room temperature. Then, the samples were further incubated in various triggering solutions for 5 min followed by thorough washing with clean PBS to remove non-adhered microparticles. The presence of the adhered microbeads was characterized by using a fluorescence microscope (LV10, Nikon) and the number of the adhered microbeads was counted by using Image-J.

Mechanical Tests

For tissue samples stored more than 10 min before mechanical tests, the samples were covered with a large amount of 0.01 w/v % sodium azide solution (in PBS) spray and sealed in plastic bags to prevent degradation and dehydration of the tissues. Unless otherwise indicated, all tissues and engineering solids were adhered to by the adhesive material after washout of the surfaces with PBS followed by 5 s pressing (with 1 kPa pressure applied by either mechanical testing machine or equivalent weight). To measure interfacial toughness, adhered samples with widths of 2.5 cm were prepared and tested by the standard 180-degree peel test (ASTM F2256) using a mechanical testing machine (2.5 kN load-cell, Zwick/Roell Z2.5). All tests were conducted with a constant peeling speed of 50 mm min$^{-1}$. The measured force reached a plateau as the peeling process entered the steady-state. Interfacial toughness was determined by dividing two times the plateau force by the width of the tissue sample (FIG. 10). Hydrophilic nylon filters (1 µm pore size, TISCH Scientific) were applied as a stiff backing for the adhesive material. Poly(methyl methacrylate) films (with a thickness of 50 µm; Goodfellow) were applied using cyanoacrylate glue (Krazy Glue) as a stiff backing for the tissues. Unless otherwise indicated, the interfacial toughness was measured 5 min after applying the triggering solution.

FTIR Characterization

Chemical composition of the adhesive material was characterized by a transmission Fourier transform infrared spectroscope (FTIR 6700, Thermo Fisher) using a Germanium attenuated total reflectance (ATR) crystal (55 deg).

In Vivo Biocompatibility Evaluation

All animal surgeries were reviewed and approved by the Committee on Animal Care at the Massachusetts Institute of Technology. Female Sprague Dawley rats (225-250 g, Charles River Laboratories) were used for all in vivo studies. Before implantation, the adhesive was prepared using aseptic techniques and was further sterilized for 3 h under UV light. For implantation in the dorsal subcutaneous space, rats were anesthetized using isoflurane (1-2% isoflurane in oxygen) in an anesthetizing chamber. Anesthesia was maintained using a nose cone. The back hair was removed and the animals were placed over a heating pad for the duration of the surgery. The subcutaneous space was accessed by a 1-2 cm skin incision per implant in the center of the animal's back. To create space for implant placement, blunt dissection was performed from the incision towards the animal shoulder blades. For the sham surgery group, no implant was placed in the subcutaneous pocket (n=4). For the triggerable detachment group, the bioadhesive (10×20 mm) was placed in the subcutaneous pocket created above the incision and detached 5 min after applying 1 mL of the triggering solution (n=4). For the bioadhesive implantation group, the bioadhesive (10 mm in width and 20 mm in length) was placed in the subcutaneous pocket created above the incision without detachment (n=4). The incision was closed using interrupted sutures (4-0 Vicryl, Ethicon) and 3-6 ml of saline were injected subcutaneously. Up to three implants were placed per animal ensuring no overlap between each subcutaneous pocket was created. After 2 weeks following the implantation, the animals were euthanized by CO$_2$ inhalation. Subcutaneous regions of interest were excised and fixed in 10% formalin for 24 h for histological analyses.

Histological Processing

Fixed tissue samples were placed into 70% ethanol and submitted for histological processing and hematoxylin and eosin (H&E) staining at the Hope Babette Tang (1983) Histology Facility in the Koch Institute for Integrative Cancer Research at the Massachusetts Institute of Technology. Histological assessment was performed by a blinded pathologist on a scale of 0-5 (0, normal or absent; 1, very mild or minimal; 2, mild; 3, moderate; 4, severe or marked; 5, very severe) to evaluate the degree of inflammation in the tissues surrounding the subcutaneous implants. The degree of acute inflammation was based on the number of neutrophils. The degree of chronic inflammation was based on the presence of lymphocytes, macrophages, and plasma cells. The degree of inflammation was evaluated based on the overall presence of indicators in each histological sample (absent, minimal, mild, moderate, or marked presence). Representative images of each group were shown in the corresponding figures.

Ex Vivo Tests

All ex vivo experiments were reviewed and approved by the Committee on Animal Care at the Massachusetts Institute of Technology. For the correction of misplaced bioadhesive, a laceration was made on a porcine lung lobe with a razor blade (3 cm in length). The air was then applied through the tubing connected to the upper part of the trachea (25 mmHg pressure) to visualize air-leakage. A bioadhesive (2.5 cm in width and 5 cm in length) was applied on the damaged lung lobe with 5 sec pressing to partially cover the laceration to represent misplacement and incomplete sealing. The misplaced bioadhesive was covered with medical gauze and the triggering solution was applied to the gauze. 5 min after the application of the triggering solution, the misplaced bioadhesive was removed by tweezers. To seal the exposed laceration, a new bioadhesive was applied to fully cover the laceration and the air-tight sealing was confirmed by cyclic inflation and deflation of the porcine lung.

For the adhesion and on-demand removal of bioadhesive device, a mock device with gold-coated polyimide and patterned bioadhesive (2 cm in width and 4 cm in length, bioadhesive pattern with 1 mm width and 1.5 mm gap) was adhered on a beating ex vivo porcine heart. An aorta of the heart was connected to tubing and programmed pressurized air inputs were introduced into the porcine heart by using a microdispenser (Ultimus™ V, Nordson EFD) to mimic heartbeats. The adhered device on the beating heart was kept for 3 hours at room temperature with continuous beating, and then checked for robust adhesion by pulling with tweezers. The bioadhesive device was covered with medical gauze and the triggering solution was applied to the gauze. 5 min after the application of the triggering solution, the bioadhesive device was removed by tweezers and the surface of the porcine heart was examined for tissue damage. To prevent dehydration and degradation, a wet towel soaked with 0.01 w/v % sodium azide solution (in PBS) was covered on the heart for experiments longer than 1 h in ambient condition.

Statistical Analysis

MATLAB software was used to assess the statistical significance of all comparison studies in this work. Data distribution was assumed to be normal for all parametric tests, but not formally tested. In the statistical analysis for comparison between multiple samples, one-way ANOVA followed by Tukey's multiple comparison test were conducted with the threshold of $*p \leq 0.05$, $p \leq 0.01$, and $*p \leq 0.001$. In the statistical analysis between two data groups, a two-sample Student's t-test was used, and the significance threshold was placed at $*p \leq 0.05$, $p \leq 0.01$, and $*p \leq 0.001$.

What is claimed is:

1. An adhesive material for adhering one or more wet surfaces and for triggerable detachment from the one or more wet surfaces comprising:
    (i) one or more hydrophilic polymers or copolymers, grafted with (ii) one or more amine coupling groups via (iii) a plurality of cleavable physical bonds and/or cleavable covalent bonds, and (iv) one or more cross linkers,
    wherein the adhesive material is in the form of a film or tape having a top surface and a bottom surface,
    wherein the adhesive material has a liquid content such that placement of one or more of the top and/or bottom surface of the adhesive material in contact with the one or more wet surfaces causes the adhesive material to absorb liquid from the one or more wet surfaces, swell to form temporary crosslinking between the adhesive material and the wet surface, and form covalent bonds between the one or more amine coupling groups and the one or more wet surfaces.

2. The adhesive material of claim 1, wherein the (i) one or more hydrophilic polymers or copolymers are selected from polyacrylic acid, polyacrylamide, polyvinyl alcohol, polyhydroxy ethyl methacrylate, polyethylene glycol, polyurethane, casein, albumin, gelatin, chitosan, hyaluronic acid, alginate, oxidized alginate, cellulose, oxidized cellulose, poly vinyl pyrrolidone, poly styrene sulfonate, collagen, pectin, and combinations thereof.

3. The adhesive material of claim 1, wherein the (ii) one or more amine coupling groups include N-hydroxysuccinimide ester, N-hydroxysulfosuccinimide ester, aldehyde, imidoester, epoxide, isocyanate, catechol, and combinations thereof.

4. The adhesive material of claim 1, wherein the (iii) cleavable physical bonds are selected from hydrogen bonds, electrostatic bonds, and host-guest bonds, and the cleavable covalent bonds are selected from boron-oxygen bonds, phenylboronate ester, disulfide bonds, hydrazone bonds, imine bonds, Diels-Alder bonds, carbon-carbon/carbon-sulfur bonds, and oxime bonds.

5. The adhesive material of claim 4, wherein the host-guest bonds are selected from αCyclodextrin(CD) as a host and n-butyl (n-Bu), Adamantyl, Benzyl, and Trans-Azobenzene groups as a guest; βCD as a host and Adamantyl, t-butyl, Cyclohexyl(ester), Cyclododecyl(amide), Benzyl, 2-Naphthylmethyl, 1-Pyrenylmethyl, Ferrocene, Trans-Azobenzene groups as a guest; and γCD as a host and Cyclododecyl, Benzyl, 2-Naphthylmethyl, 9-Phenanthrylmethyl, and 1-Pyrenylmethyl groups as a guest.

6. The adhesive material of claim 1, wherein the (iv) one or more crosslinkers are selected from gelatin methacrylate, hyaluronic acid methacrylate, oxidized methacrylic alginate, polycaprolactone diacrylate, N,N'-bis(acryloyl) cystamine, N,N'-methylenebis(acrylamide), polyethylene glycol diacrylate, polyethylene glycol dimethacrylate, and combinations thereof.

7. The adhesive material of claim 1, further comprising interpenetrating networks of (i) polyvinyl alcohol (PVA) and poly(acrylic acid) (PAA) grafted with (ii) N-hydroxysuccinimide (NHS) ester via (iii) cleavable disulfide bonds in the dry state.

8. The adhesive material of claim 7, wherein negatively charged carboxylic acid groups in the poly(acrylic acid) grafted with N-hydroxysuccinimide ester facilitate absorption of liquid and swelling of the dry adhesive material and further form intermolecular bonds with the one or more wet surfaces within less than 60 seconds after contact between the dry adhesive material and the one or more wet surfaces.

9. The adhesive material of claim 7, wherein the N-hydroxysuccinimide ester grafted in the poly(acrylic acid) forms cleavable covalent bonds with primary amine groups present on the one or more wet surfaces.

10. The dry adhesive material of claim 1, wherein after the covalent crosslinking is formed between the one or more amine coupling groups and the one or more wet surfaces, the swollen adhesive material transforms into a layer of a hydrogel.

11. The adhesive of claim 10, wherein the hydrogel has a fracture toughness of at least about $1,000$ J m$^{-2}$.

12. The adhesive material of claim 1 in the form of a flat sheet, a perforated sheet, a double sided tape or film, or a perforated double sided tape or film.

13. The adhesive material of claim 12, wherein the adhesive material comprises a top surface and a bottom surface, and wherein adhesive material further comprises one or more backing material layers disposed on at least one of the top surface and bottom surface.

14. The adhesive material of claim 1, further comprising one or more engineering solids, and/or devices adhered to one or more surfaces of the adhesive material.

15. The adhesive material of claim 1, wherein the adhesive material is biodegradable.

* * * * *